United States Patent
Leonard et al.

(10) Patent No.: US 10,407,478 B2
(45) Date of Patent: *Sep. 10, 2019

(54) ANTI-TUMOR PROPERTIES OF DICKKOPF 3B

(71) Applicant: University of Massachusetts, Boston, MA (US)

(72) Inventors: Jack L. Leonard, Shrewsbury, MA (US); Deborah M. Leonard, Shrewsbury, MA (US); Karl J. Simin, Princeton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,334

(22) Filed: May 17, 2016

(65) Prior Publication Data

US 2016/0326225 A1    Nov. 10, 2016

Related U.S. Application Data

(63) Continuation of application No. 14/511,667, filed on Oct. 10, 2014, which is a continuation of application No. PCT/US2013/031118, filed on Mar. 14, 2013.

(60) Provisional application No. 61/615,514, filed on Mar. 26, 2012.

(51) Int. Cl.

| | | |
|---|---|---|
| *C12N 15/09* | (2006.01) | |
| *C12N 15/62* | (2006.01) | |
| *C12N 15/63* | (2006.01) | |
| *C07K 1/00* | (2006.01) | |
| *C07K 19/00* | (2006.01) | |
| *C07K 14/47* | (2006.01) | |
| *A61K 38/17* | (2006.01) | |
| *A61K 35/76* | (2015.01) | |
| *A01K 67/027* | (2006.01) | |
| *C07K 14/82* | (2006.01) | |
| *C07K 14/00* | (2006.01) | |
| *A61K 38/00* | (2006.01) | |

(52) U.S. Cl.
CPC ...... *C07K 14/4703* (2013.01); *A01K 67/0276* (2013.01); *A61K 35/76* (2013.01); *A61K 38/1709* (2013.01); *C07K 14/00* (2013.01); *C07K 14/82* (2013.01); *A01K 2217/075* (2013.01); *A01K 2217/15* (2013.01); *A01K 2217/203* (2013.01); *A01K 2227/105* (2013.01); *A01K 2267/0331* (2013.01); *A01K 2267/0393* (2013.01); *A61K 38/00* (2013.01); *C07K 2319/10* (2013.01); *C07K 2319/21* (2013.01); *C12N 2740/15043* (2013.01)

(58) Field of Classification Search
None
See application file for complete search history.

(56) References Cited

PUBLICATIONS

Iea et al High efficiency protein transduction of quiescent and proliferating primary hematopoietic cells J. Biochem. Biophys. Methods 55 (2003) 251-258.*
Nagahara et al Transduction of full-length TAT fusion proteins into mammalian cells: TAT-p27Kip1 induces cell migration Nature Medicine • vol. 4 • No. 12 • Dec. 1998 pp. 1449-1457.*
Lindgren et al, Cell-penetrating peptides TiPS—Mar. 2000 (vol. 21) 99-103.*
Start codon—Wikipedia; pp. 1-4; downloaded on Jul. 18, 2018.*
NCBI DKK3 dickkopf WNT signaling pathway inhibitor 3 [ *Homo sapiens* (human) ] Gene ID: 27122, updated on Jul. 8, 2018 pp. 1-11.*
Lorsy et al. 2016 Loss of Dickkopf 3 Promotes the Tumorigenesis of Basal Breast Cancer pp. 1-17.*
Farwell, A.P., et al., "Identification of a 27-kDa Protein with the Properties of Type II Iodothyronine 5'-Deiodinase in Dibutyryl Cyclic AMP-Stimulated Glial Cells," The Journal of Biological Chemistry, vol. 264(34), pp. 20561-20567 (1989).
Leonard, D., et al., "Cloning, Expression, and Functional Characterization of the Substrate Binding Subunit of Rat Type II Iodothyronine 5-Deiodinase,"The Journal of Biological Chemistry, vol. 275(33); pp. 25194-25201 (2000).
Leonard, J., et al., "The Dkk3 Gene Encodes a Vital Intracellular Regulator of Cell Proliferation," PLOS One 12(7): e0181724, pp. 1-27 (2017).
Marciniak, R.A., et al., "HIV-1 Tat Protein Trans-Activates Transcription in Vitro," Cell, vol. 63, pp. 791-802 (1990).
Green, M., et al., "Autonomous Functional Domains of Chemically Synthesized Human Immunodeficiency Virus Tat Trans-Activator Protein," Cell, vol. 55, pp. 1179-1188 (1988).
Vives, E., et al., "A Truncated HIV-1 Tat Protein Basic Domain Rapidly Translocates Through the Plasma Membrane and Accumulates in the Cell Nucleus," The Journal of Biological Chemistry, vol. 272(25): pp. 16010-16017 (1997).
Milletti, F., "Cell-Penetrating Peptides: Classes, Origin, and Current Landscape," Drug Discovery Today, vol. 17 (15/16) 2012.
Ho, A., et al., "Synthetic Protein Transduction Domains: Enhanced Transduction Potential in Vitro and in Vivo," Cancer Research 61, pp. 474-477 (2001).
Guidotti, G., et al., "Cell-Penetrating Peptides: from Basic Research to Clinics," Trends in Pharmacological Sciences, vol. 38(4): pp. 406-424 (2017).

(Continued)

*Primary Examiner* — Maria G Leavitt
(74) *Attorney, Agent, or Firm* — Fish & Richardson P.C.

(57) ABSTRACT

The invention relates to novel therapeutic approaches to cancer treatment that exploits tumor suppressor functions of DKK3b by site-specific delivery of DKK3b. Novel therapeutics and methods for treating tumors and cancers utilizing DKK3b tumor suppressor functions are disclosed.

9 Claims, 22 Drawing Sheets

Specification includes a Sequence Listing.

(56) References Cited

PUBLICATIONS

Krupnik, V.E., et al., "Functional and Structural Diversity of the Human Dickkopf Gene Family," Gene 238; pp. 301-313 (1999).

Wadia, J.S., et al., Protein Transduction Technology, Current Opinion in Biotechnology, 13: pp. 52-56 (2002).

Kobayashi, K., et al., "Reduced Expression of the REIC/Dkk-3 Gene by Frornotor-Hypermethylation in Human Tumor Cells," Gene 282: pp. 151-158 (2002).

* cited by examiner

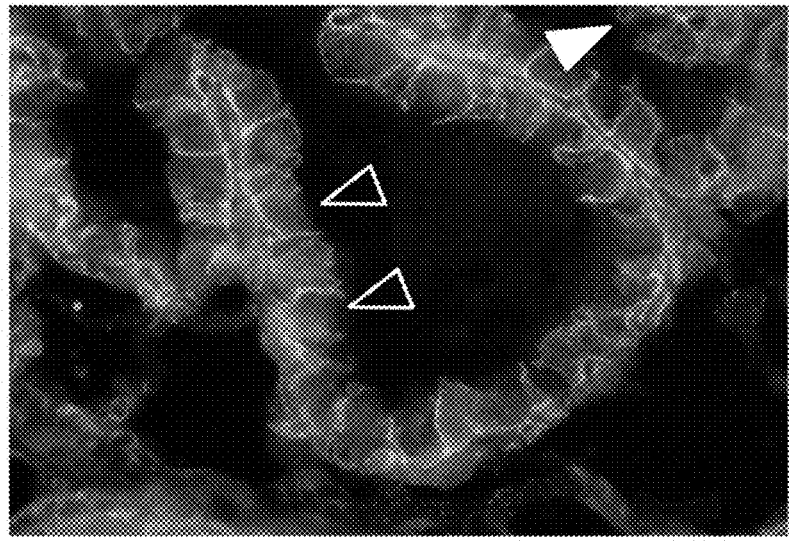
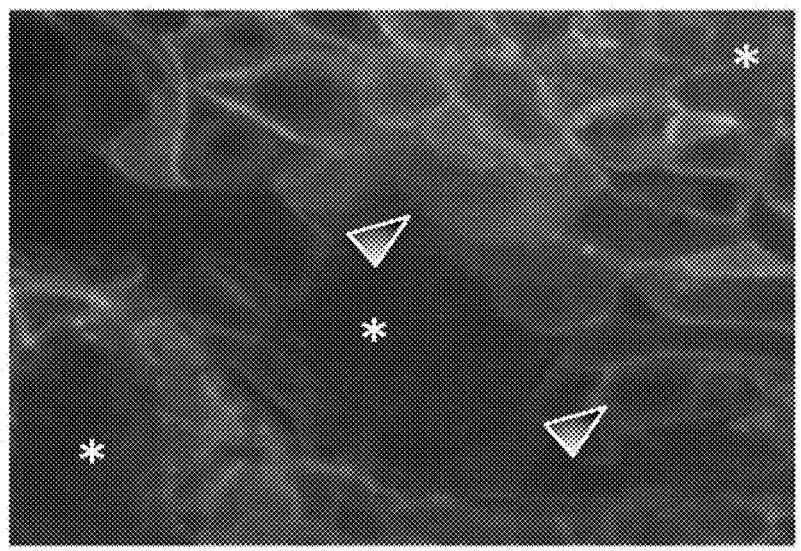
FIG. 6

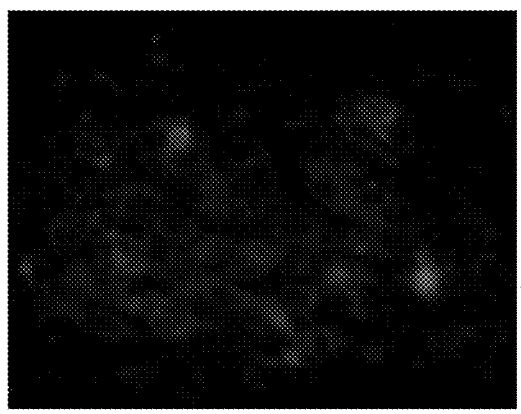 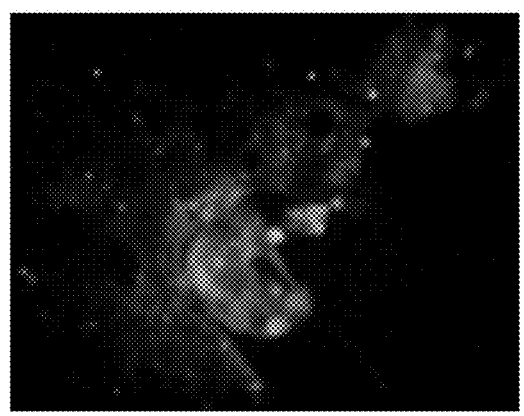
FIG. 12

Optimized PTD Plus strand

5'-GATCCAAGCTTGGCTATGCTCGCGCTGCTGCTGCTCAGGCTCGCGCTGGTGGATCCAC-3' (SEQ ID NO:6)

Optimized PTD minus strand

5'-CATGGTGGATCCACCAGCGCGAGCCTGAGCAGCAGCAGCGCGAGCATAGCCAAGCTTG-3' (SEQ ID NO:8)

Sequence: PTD_domain_cDNA_sequence Range: 1 to 60

```
       10        20        30        40        50        60
GATCCAAGCTTGGCTATGCTCGCGCTGCTGCTGCTCAGGCTCGCGCTGGTGGATCCAC         (SEQ ID NO:6)
    GTTCGAACCGATACGAGCGCGACGACGACGAGTCCGAGCGCGACCACCTAGGTGGTAC     (SEQ ID NO:8)
     S  K  L  G  Y  A  R  A  A  A  A  Q  A  R  A  G  G  S  T  M>   (SEQ ID NO:7)
        ___TRANSLATION OF PTD DOMAIN CDNA SEQUENCE [___>
```

Annealed PTD domain from synthesized primers (SEQ ID NOS:6 and 8)

```
         GA TCC AAG CTT GGC TAT GCT CGC GCT GCT GCT GCT GCT GCT CGC GCT GGT GGA TCC AC  NcoI -3'
            G TTC GAA CCG ATA CGA GCG CGA CGA CGA CGA GTC GCA GCG CGA CCA CCT AGG TGG TAC
BamH1    S   K   L   G   Y   A   R   A   A   A   A   Q   A   R   A   G   G   S   T   M
```

(SEQ ID NO:7)

FIG. 16

*Map of N-terminus of the "optimal" PTD-DKK3b fusion protein.* (synthetic PTD domain is underlined)

*T7 promoter*

```
10        20        30        40        50        60        70        80        90
100
GATCTCGATCCCGCGAAATTAATACGACTCACTATAGGGAGACCACAACGGTTTCCCTCTAGATAATTTTGTTTAACTTTAAGAAGGAGATATACA
T (SEQ ID NO:9)
```

*Start*                *6-His tag*                      *T7 gene 10 Leader*

```
             110       120       130       140       150       160       170
 ATG CGG GGT TCT CAT CAT CAT CAT CAT CAT GGT ATG GCT AGC ATG ACT GGT GGA CAG CAA ATG GGT CGG (SEQ
ID NO:9, continued)

M   R   G   S   H   H   H   H   H   H   G   M   A   S   M   T   G   G   Q   Q   M   G   R  (SEQ
ID NO:10)
```

*Xpress™ epitope/enterokinase site*         *Protein transduction domain (PTD)*

```
            180       190       200       210       220       230
240
 GAT CTG TAC GAC GAT GAC GAT AAG|GAT CGA TGG GGA TCC AAG CTT GGC TAT GCT CGC GCT GCT GCT GCT CAG
GCT CGC GCT  (SEQ ID NO:9, continued)

D   L   Y   D   D   D   D   K | D   R   W   G   S   K   L   G   Y   A   R   A   A   A   A   Q
  A   R   A  (SEQ ID NO:10, continued)
```

*Human DKK3b*

```
250       260
 GGT GGA TCC ACC ATG GAG GCA GAA GAA GCT GCT  (SEQ ID NO:9, continued)

G   G   S   T   M   E   A   E   E   A   A   (SEQ ID NO:10, continued)
```

FIG. 17

*PRIMERS FOR IN-FRAME CLONING OF DKK3B (MOUSE AND HUMAN)*

5' end of dkk3b NcoI site for in-frame cloning

Mouse dkk3b 5'GATCCTGA ACC ATG GAG GCG GAA GAA GCA G  (SEQ ID NO:11)

Human dkk3b 5'GATCCTGA ACC ATG GAG GCA GAA GAA GCT G  (SEQ ID NO:12)

3'end of dkk3b added XhoI site for cloning human5' GATCCTGACTCGAGTTACTAAATCTCTTCCCCTCCCAGCAGTG  (SEQ ID NO:13)

in lab mouse5' GATCCTGACTCGAGTTACTAAATCTCCTCCTCTCCGCCTAG  (SEQ ID NO:14)

FIG. 21

SEQUENCE LISTING

```
<160> NUMBER OF SEQ ID NOS: 14

<210> SEQ ID NO 1
<211> LENGTH: 96
<212> TYPE: DNA
<213> ORGANISM: Unknown
<220> FEATURE:
<223> OTHER INFORMATION: synthesized

<400> SEQUENCE: 1
atctcgatcc cgcgaaatta atacgactca ctatagggag accacaacgg tttccctcta      60
gataattttg tttaacttta agaaggagat atacat                               96

<210> SEQ ID NO 2
<211> LENGTH: 207
<212> TYPE: DNA
<213> ORGANISM: Unknown
<220> FEATURE:
<223> OTHER INFORMATION: synthesized with TAT-domain and restriction
      sites
<220> FEATURE:
<221> NAME/KEY: CDS
<222> LOCATION: (1)..(207)

<400> SEQUENCE: 2 atg cgg ggt tct cat cat cat cat cat cat ggt atg gct agc atg act         48
Met Arg Gly Ser His His His His His His Gly Met Ala Ser Met Thr
1               5                   10                  15 ggt gga cag caa atg ggt cgg gat ctg tac gac gat gac gat aag gat         96
Gly Gly Gln Gln Met Gly Arg Asp Leu Tyr Asp Asp Asp Asp Lys Asp
            20                  25                  30 cga tgg gga tcc aag ctt ggc tac ggc cgc aag aaa cgc cgc cag cgc        144
Arg Trp Gly Ser Lys Leu Gly Tyr Gly Arg Lys Lys Arg Arg Gln Arg
        35                  40                  45 cgc cgc ggt gga tcc acc atg gcc ggt acc ggt ctc gag gtg cat gcg        192
Arg Arg Gly Gly Ser Thr Met Ala Gly Thr Gly Leu Glu Val His Ala
    50                  55                  60 gtg aat tcg aag ctt                                                    207
Val Asn Ser Lys Leu
65

<210> SEQ ID NO 3
<211> LENGTH: 69
<212> TYPE: PRT
<213> ORGANISM: Unknown
<220> FEATURE:
<223> OTHER INFORMATION: Synthetic Construct
```

```
<400> SEQUENCE: 3

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Arg Gln Arg
            35                  40                  45

Arg Arg Gly Gly Ser Thr Met Ala Gly Thr Gly Leu Glu Val His Ala
        50                  55                  60

Val Asn Ser Lys Leu
65

<210> SEQ ID NO 4
<211> LENGTH: 50
<212> TYPE: DNA
<213> ORGANISM: unknown
<220> FEATURE:
<223> OTHER INFORMATION: synthesized HA tag
<220> FEATURE:
<221> NAME/KEY: CDS
<222> LOCATION: (3)..(50)

<400> SEQUENCE: 4 cc atg tcc ggc tat cca tat gac gtc cca gac tat gct ggc tcc atg        47
   Met Ser Gly Tyr Pro Tyr Asp Val Pro Asp Tyr Ala Gly Ser Met
   1               5                   10                  15 ggc                                                                    50
Gly

<210> SEQ ID NO 5
<211> LENGTH: 16
<212> TYPE: PRT
<213> ORGANISM: unknown
<220> FEATURE:
<223> OTHER INFORMATION: Synthetic Construct

<400> SEQUENCE: 5

Met Ser Gly Tyr Pro Tyr Asp Val Pro Asp Tyr Ala Gly Ser Met Gly
1               5                   10                  15

<210> SEQ ID NO 6
<211> LENGTH: 58
<212> TYPE: DNA
<213> ORGANISM: unknown
<220> FEATURE:
<223> OTHER INFORMATION: synthesized PTD Plus strand
<220> FEATURE:
<221> NAME/KEY: CDS
<222> LOCATION: (3)..(56)

<400> SEQUENCE: 6 ga tcc aag ctt ggc tat gct cgc gct gct gct gct cag gct cgc gct        47
   Ser Lys Leu Gly Tyr Ala Arg Ala Ala Ala Ala Gln Ala Arg Ala
   1               5                   10                  15 ggt gga tcc ac                                                         58
Gly Gly Ser <210> SEQ ID NO 7
<211> LENGTH: 18
<212> TYPE: PRT
<213> ORGANISM: unknown
<220> FEATURE:
<223> OTHER INFORMATION: Synthetic Construct

<400> SEQUENCE: 7
```

```
Ser Lys Leu Gly Tyr Ala Arg Ala Ala Ala Gln Ala Arg Ala Gly
1               5                  10                  15

Gly Ser

<210> SEQ ID NO 8
<211> LENGTH: 58
<212> TYPE: DNA
<213> ORGANISM: unknown
<220> FEATURE:
<223> OTHER INFORMATION: synthesized PTD minus strand

<400> SEQUENCE: 8
catggtggat ccaccagcgc gagcctgagc agcagcagcg cgagcatagc caagcttg      58

<210> SEQ ID NO 9
<211> LENGTH: 280
<212> TYPE: DNA
<213> ORGANISM: unknown
<220> FEATURE:
<223> OTHER INFORMATION: synthesized
<220> FEATURE:
<221> NAME/KEY: CDS
<222> LOCATION: (98)..(280)

<400> SEQUENCE: 9
gatctcgatc ccgcgaaatt aatacgactc actataggga gaccacaacg gtttccctct      60
agataatttt gtttaacttt aagaaggaga tatacat atg cgg ggt tct cat cat     115
                                        Met Arg Gly Ser His His
                                          1               5 cat cat cat cat ggt atg gct agc atg act ggt gga cag caa atg ggt      163
His His His His Gly Met Ala Ser Met Thr Gly Gly Gln Gln Met Gly
             10                  15                  20 cgg gat ctg tac gac gat gac aag gat cga tgg gga tcc aag ctt          211
Arg Asp Leu Tyr Asp Asp Asp Lys Asp Arg Trp Gly Ser Lys Leu
         25                  30                  35 ggc tat gct cgc gct gct gct gct cag gct cgc gct ggt gga tcc acc      259
Gly Tyr Ala Arg Ala Ala Ala Ala Gln Ala Arg Ala Gly Gly Ser Thr
     40                  45                  50 atg gag gca gaa gaa gct gct                                          280
Met Glu Ala Glu Glu Ala Ala
55                  60

<210> SEQ ID NO 10
<211> LENGTH: 61
<212> TYPE: PRT
<213> ORGANISM: unknown
<220> FEATURE:
<223> OTHER INFORMATION: Synthetic Construct

<400> SEQUENCE: 10

Met Arg Gly Ser His His His His His His Gly Met Ala Ser Met Thr
1               5                  10                  15

Gly Gly Gln Gln Met Gly Arg Asp Leu Tyr Asp Asp Asp Lys Asp
             20                  25                  30

Arg Trp Gly Ser Lys Leu Gly Tyr Ala Arg Ala Ala Ala Ala Gln Ala
         35                  40                  45

Arg Ala Gly Gly Ser Thr Met Glu Ala Glu Glu Ala Ala
     50                  55                  60

<210> SEQ ID NO 11
<211> LENGTH: 30
<212> TYPE: DNA
```

```
<213> ORGANISM: artificial sequence
<220> FEATURE:
<223> OTHER INFORMATION: synthesized with partly mouse sequence

<400> SEQUENCE: 11
gatcctgaac catggaggcg aagaagcag                                    30

<210> SEQ ID NO 12
<211> LENGTH: 30
<212> TYPE: DNA
<213> ORGANISM: artificial sequence
<220> FEATURE:
<223> OTHER INFORMATION: synthesized with partly human sequence

<400> SEQUENCE: 12
gatcctgaac catggaggca gaagaagctg                                   30

<210> SEQ ID NO 13
<211> LENGTH: 43
<212> TYPE: DNA
<213> ORGANISM: artificial sequence
<220> FEATURE:
<223> OTHER INFORMATION: synthesized with partly human sequence

<400> SEQUENCE: 13
gatcctgact cgagttacta aatctcttcc cctcccagca gtg                    43

<210> SEQ ID NO 14
<211> LENGTH: 41
<212> TYPE: DNA
<213> ORGANISM: artificial sequence
<220> FEATURE:
<223> OTHER INFORMATION: synthesized with partly mouse sequence

<400> SEQUENCE: 14
gatcctgact cgagttacta aatctcctcc tctccgccta g                      41
```

ANTI-TUMOR PROPERTIES OF DICKKOPF 3B

PRIORITY CLAIMS AND RELATED PATENT APPLICATIONS

This application claims the benefit of priority from and is a continuation application of U.S. patent application Ser. No. 14/511,667, filed Oct. 10, 2014, which claims the benefit of priority, under 35 USC 120, from the US designation of International Application No. PCT/US13/31118, filed on Mar. 14, 2013, which claims benefit of priority from U.S. Provisional Application Ser. No. 61/615,514, filed on Mar. 26, 2012, the entire content of which is incorporated herein by reference in its entirety for all purposes.

GOVERNMENT RIGHTS

This invention was made with Government support under grant nos. DK038772 and DK060051 awarded by the National Institutes of Health. The Government has certain rights in the invention.

TECHNICAL FIELD OF THE INVENTION

The invention generally relates to tumor suppressor properties and functions of DKK3b and anti-tumor applications and uses thereof. More particularly, the invention relates to novel therapeutics and methods for treating tumors and cancers utilizing DKK3b tumor suppressor functions, for example, via site-specific delivery of DKK3b or a related agent.

BACKGROUND OF THE INVENTION

Suppressed Dickkopf-3 (DKK3) expression is a hallmark of many human cancers and expression levels are inversely related to tumor virulence (e.g., in prostate cancer and ovarian cancer). Using prostate cancer as an example, overexpression of DKK3 halts proliferation of prostate cancer cells, but the beneficial consequences of DKK3 over-expression in both in vivo and ex vivo models of prostate cancer are likely an artifact of the inadvertent initiation of an ER stress response in cells attempting to process an over-expressed, exogenous, secretory gene product. (Abarzua, et al. 2005 *Cancer Res* 65 (21): 9617-22; Abarzua, et al. 2008 *Biochem Biophys Res Commun* 375 (4): 614-8; Abarzua, et al. 2007 *Int J Mol Med* 20 (1): 37-43.)

The tumor suppressor activity of DKK3 was also reported to be due to its ability to block the translocation of β-catenin to the nucleus by forming an inactive complex composed of a cytoplasmic ~30 kDa DKK3 gene product and βTrCP. (Lee, et al. 2009 *Int J Cancer* 124 (2): 287-97.) Since it is unlikely that chronic ER stress is the mechanism by which endogenous DKK3 gene products influence normal cell proliferation, the identification of a non-secreted, intracellular version of DKK3 and the discovery of two intracellular events (JNK activation and β-catenin inactivation) that facilitate growth arrest offer an opportunity to define the molecular events mediating the DKK3 tumor suppressor function in the prostate.

Early studies by Dr. Leonard and colleagues discovered that the DKK3 gene locus encodes a second transcript that produces an intracellular membrane associated 29 kDa protein (formally D2p29, now renamed, DKK3b). (Leonard, et al. 2000 *J Biol Chem* 275 (33): 25194-201; Farwell, et al. 1996 *J Biol Chem* 271 (27): 16369-74; Safran, et al. 1996 *J Biol Chem* 271 (27): 16363-8; Farwell, et al. 1993 *J Biol Chem* 268 (7): 5055-62.)

Subsequent studies revealed that this DKK3b gene product originated from a second transcriptional start site located in intron 2. Dkk3b was originally identified in astrocytes as a highly trafficked membrane protein that binds thyroid hormone with high affinity. Analysis of the DKK3 gene locus revealed that DKK3b is encoded by exons 3-8 and that a functional transcriptional start site—with a TATA box—is located in intron 2 (FIG. 1A). Promoter mapping studies narrowed the promoter activity to ~250 bases upstream of exon 3. Deletion of the TATA box blocked promoter function. ChIP analysis revealed that this promoter was functional in vivo (FIG. 1B).

Importantly, in both the full length DKK3 and truncated DKK3b mRNAs, the only authentic Kozak start site is located at the Met beginning at exon 3, and in vitro translation of the full-length DKK3a mRNA using Kozak context dependent conditions yields a 29 kDa protein. (Leonard, et al. 2000 *J Biol Chem* 275 (33): 25194-201.) Real time PCR analysis of DKK3 locus transcripts revealed that the DKK3a transcript (exons 2-8) accounted for ~55% of the total DKK3 mRNAs, while the DKK3b transcript (exons 3-8) contributed ~45% of the total DKK3 mRNAs. In the ΔDKK3 mouse that lacks exons 2, full-length DKK3a transcripts are lost, but the DKK3b mRNA is preserved (FIG. 1C). (Barrantes, et al. 2006 *Mol Cell Biol* 26 (6): 2317-26.) Affinity labeling of DKK3b associated with the cellular membranes of ΔDKK3 mouse brain yielded the anticipated immunoreactive DKK3b, while a full-length glycosylated DKK3 was not synthesized (FIG. 3D). (Farwell, et al. 1989 *J Biol Chem* 264 (34): 20561-7.) These data demonstrate that the DKK3 locus encodes two functional transcripts; one encoding a secreted glycoprotein identified as DKK3a, and another an intracellular 29 kDa DKK3b protein.

There remains an ongoing need for establishing novel therapeutic approaches to cancer treatment utilizing DKK3b tumor suppressor function, for example, treatment methodologies and pharmaceutical compositions that can arrest the growth of various cancers, such as ovarian and prostate cancers.

BRIEF DESCRIPTION OF THE DRAWINGS

FIG. 6 depicts exemplary DKK3b and β-catenin expression at early and late stages of mammary tumor formation in TBP mouse. Hollow arrow, normal epithelium; solid arrow, early tumor cells; shaded arrow, β-catenin high/DKK3b low; asterisk, DKK3b high/β-catenin low.

FIG. 12 depicts exemplary C8DKK3b$^{CFP+/-}$ cells grown for 72 h with the methylase inhibitor 5'azacytidine.

FIG. 16 depicts exemplary optimized PTD Plus strand; Optimized PTD minus strand; Annealed PTD domain from synthesized primers.

FIG. 17 depicts exemplary map of N-terminus of the "optimal" PTD-DKK3b fusion protein.

FIG. 21 depicts exemplary primers for in-frame cloning of DKK3B (mouse and human).

SUMMARY OF THE INVENTION

Figure 1:
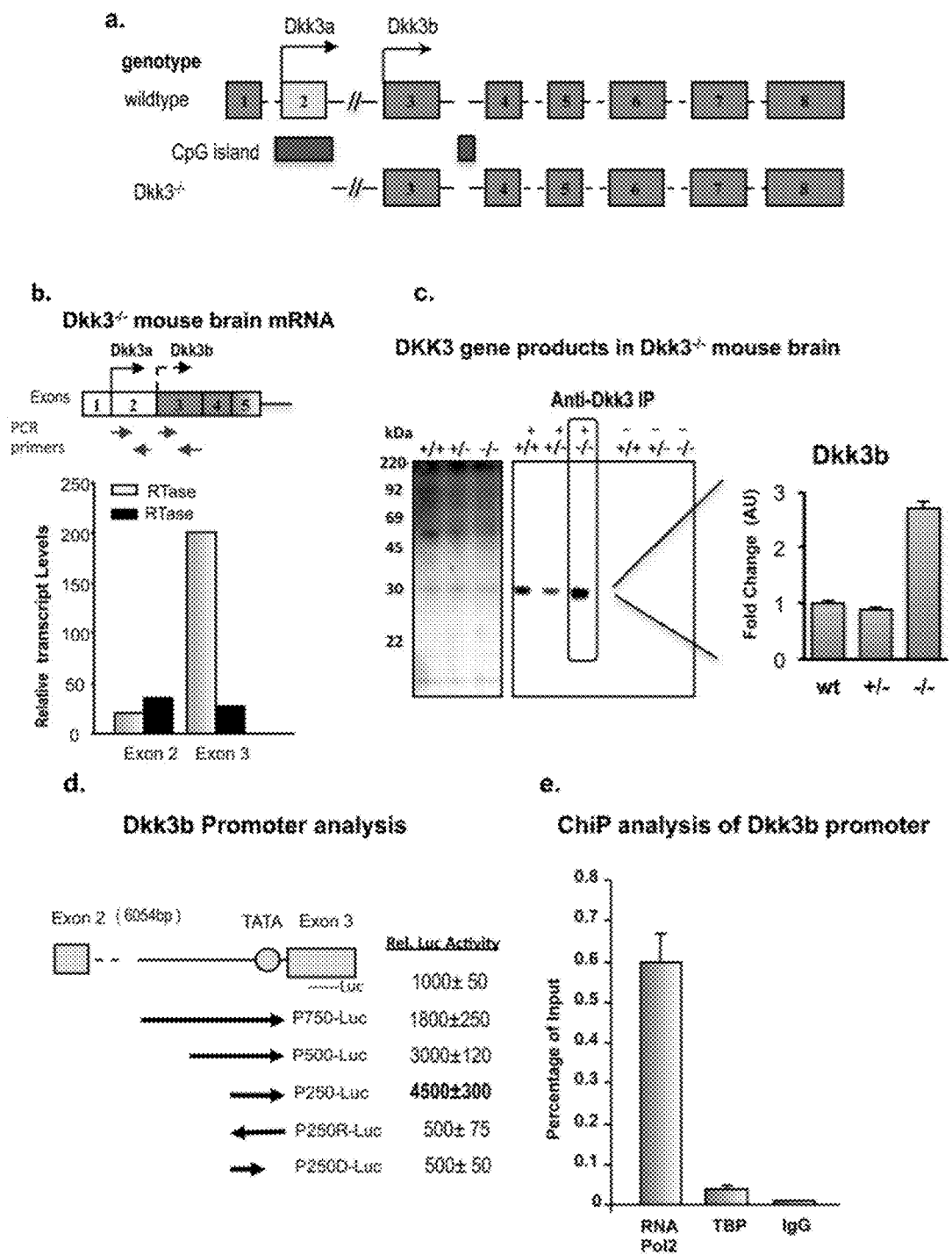
FIG. 1 depicts exemplary characterization of the mouse Dkk3 gene.

The invention provides novel therapeutic approaches to cancer treatment that exploits tumor suppressor functions of DKK3b. A novel tumor suppressor has been identified that originates from an internal transcription start site of the Dkk3 gene locus that harbors all of the anti-cancer properties. Rather than the current therapeutic efforts that are all directed at an artifactual ER stress response due to exogenous expression of the full length secreted and glycosylated DKK3 gene product, the present invention is promised to bring a unique approach that changes the direction of the field.

In one aspect, the invention generally relates to the identified human DKK3b protein.

In another aspect, the invention generally relates to a recombinant virus genetically modified to express human DKK3b protein.

In yet another aspect, the invention generally relates to an isolated nucleic acid molecule comprising a polynucleotide sequence that encodes DKK3b protein.

In yet another aspect, the invention generally relates to a recombinant transgene comprising a polynucleotide that encodes DKK3b protein.

In yet another aspect, the invention generally relates to an isolated recombinant human DKK3b protein.

In yet another aspect, the invention generally relates to host cell transformed with an isolated recombinant human DKK3b protein.

In yet another aspect, the invention generally relates to a pharmaceutical composition comprising a recombinant virus genetically modified to express human DKK3b protein and a pharmaceutically acceptable carrier.

In yet another aspect, the invention generally relates to a method for treating cancer or inhibiting tumor progression in a subject in need thereof, comprising administering to the subject a pharmaceutical composition comprising a recombinant virus genetically modified to express human DKK3b protein and a pharmaceutically acceptable carrier.

In yet another aspect, the invention generally relates to a pharmaceutical composition comprising human DKK3b protein and a pharmaceutically acceptable carrier.

In yet another aspect, the invention generally relates to a method for treating cancer or inhibiting tumor progression in a subject in need thereof, comprising administering to the subject a pharmaceutical composition comprising DKK3b protein.

In yet another aspect, the invention generally relates to a method for inducing a tumor-suppression effect in a subject in need thereof, comprising administering to the subject a pharmaceutical composition comprising DKK3b protein.

Cancer that may be therapeutically treated according to the disclosed invention can be any type of cancer, including carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

DETAILED DESCRIPTION OF THE INVENTION

The invention relates to novel therapeutic approaches to cancer treatment that exploit the tumor suppressor functions of DKK3b. More particularly, a novel tumor suppressor has been identified that originates from an internal transcription start site of the Dkk3 gene locus and this gene product harbors all of the anti-cancer properties of this gene. Rather than the current therapeutic efforts that are all directed at an artifactual ER stress response due to exogenous expression of the full length secreted and glycosylated DKK3 gene product, the present invention is promised to bring a unique approach that will change the direction of the field.

Unchecked signaling by the Wnt pathway signaling molecule, β-catenin, is common in cancer and the Dickkopf-related protein 3 (DKK3) is one of the most promising tumor suppressor molecule(s) that controls β-catenin levels. Tumor malignancy is inversely related to DKK3 levels and over-expression arrests cell proliferation in nearly all cancer cells. Even though DKK3 does not block receptor activation by Wnt, the anticancer actions of the secreted DKK3 glycoprotein are widely presumed to be due to inhibition of the Wnt receptor complex. However, recent reports challenge this conventional view of DKK3 action. Yeast two-hybrid analysis revealed that DKK3 interacted with the ubiquitin ligase, β-transducin repeats containing protein (β TrCP) and subsequent co-immunoprecipitation studies identified DKK3 as part of an intracellular complex with (β TrCP) and β-catenin that prevents β-catenin nuclear translocation. DKK3 was also shown to activate the N-terminal Jun kinase (JNK) stress pathway leading to cancer cell loss. These findings illustrate an important role for intracellular signaling by DKK3. We recently discovered that the Dkk3 locus encodes two gene products, a secreted glycoprotein (DKK3a) that does not impact Wnt signaling, and a novel, intracellular protein, DKK3b, which inhibits Wnt signaling. We propose that the intracellular DKK3b is responsible for the published anti-cancer effects of this tumor suppressor and acts by blocking the nuclear import of β-catenin and increasing cell death, two fundamental cellular events that arrest tumor growth and propagation.

The Molecular Mechanism of DKK3b Action

There is general agreement that 1) Dkk3 expression levels are inversely related to tumor malignancy, and that 2) DKK3 over-expression halts cancer cell proliferation. (Lodygin, et al. 2005 *Cancer Res* 65 (10):4218-4227; Veeck, et al. 2008 *Breast Cancer Res* 10 (5):R82; Veeck, et al. 2012 *Biochim Biophys Acta* 1825 (1):18-28; Yue, et al. 2008 *Carcinogenesis* 29 (1):84-92; Edamura, et al. 2007 *Cancer Gene Ther* 14 (9):765-772; Gu, et al. 2011 *World J Gastroenterol* 17 (33):3810-3817; Medinger, et al. 2011 *Thrombosis and haemostasis* 105 (1):72-80; Pei, et al. 2009 *Virchows Arch* 454 (6):639-646.) Despite these findings, the mechanism(s) of DKK3 action remain completely unknown. Unlike other DKK family members, DKK3 does not bind to the Wnt receptor complex. (Niehrs, et al. 2006 *Oncogene* 25 (57): 7469-7481; Barrantes, et al. 2006 *Mol Cell Biol* 26 (6):2317-2326.) Moreover, deletion of mouse Dkk3 gene produced a benign phenotype with no increase in tumor formation.

Our discovery of a novel intracellular DKK3 gene product, DKK3b (previously named D2p29), produced from transcripts originating from an internal start site, redefines and reconciles these disparate observations. (Leonard, et al. 2000 *J Biol Chem* 275 (33):25194-25201.) DKK3b possesses all the anti-tumor effects previously ascribed to DKK3a. In fact, the targeting strategy used to delete the mouse Dkk3 ablated only DKK3a, leaving DKK3b untouched, thus explaining the lack of increased tumorigenesis. (Barrantes, et al. 2006 *Mol Cell Biol* 26 (6):2317-2326.) Recent studies show that DKK3 specifically binds to the E3 ubiquitin ligase component, β-transducin repeat containing protein (βTrCP), and that this complex in turn binds unphosphorylated β-catenin preventing its nuclear import. (Lee, et al. 2009 *Int J Cancer* 124 (2):287-297; Hoang, et al. 2004 *Cancer Res* 64 (8):2734-2739.) Since the membrane barrier makes it improbable that the secreted DKK3a glycoprotein acts inside the cell by direct association with E3 ubiquitin ligase machinery, the novel DKK3b gene product becomes the likely tumor suppressor responsible for attenuating Wnt signaling. Understanding the details of how DKK3b arrests tumor growth offers a real opportunity to develop effective therapeutics that defeat oncogenesis at its source.

The present invention defines the molecular mechanism(s) of DKK3b tumor suppressor function using both prostate and breast cancer cells as models for cancers in general and addresses the anti-tumor effects of site-specific delivery of DKK3b. By re-directing the focus of work to the authentic important tumor suppressor, the invention establishes an important foundation for rational therapeutic approaches to cancer treatment.

In silico analysis revealed that DKK3b was encoded by exons 3-8 of the Dkk3 gene, and the presence of this novel DKK3 gene product in brains from the Dkk3$^{-/-}$ mouse provided insight into its origins. (Barrantes, et al. 2006 *Mol Cell Biol* 26 (6):2317-2326.) Deletion of exon 2 from the mouse Dkk3 locus (FIG. 1*a*) clearly eliminated expression of DKK3a, but does not affect DKK3b transcripts starting at exon 3 (FIG. 1*b*) and led to a nearly 3-fold increase in the ~30 kDa DKK3b protein (FIG. 1*c*). Promoter activity was localized to ~250 bases upstream of exon 3, and deletion of the TATA box blocked promoter function. ChIP analysis showed that the DKK3b promoter was functional in vivo (FIG. 1*d*, 1*e*). QPCR using exon 2 and exon 3 specific DKK3 primer sets found that the DKK3a transcript (exons 2-8) accounted for 50-55% of the mRNA in primary cells, while the DKK3b transcript (exons 3-8) contributed ~45% of the total. These data show that the Dkk3 gene encodes two functional transcripts: one encoding a ~60 kDa secreted glycoprotein DKK3a; and a second 30 kDa intracellular protein, DKK3b.

Figure 2:
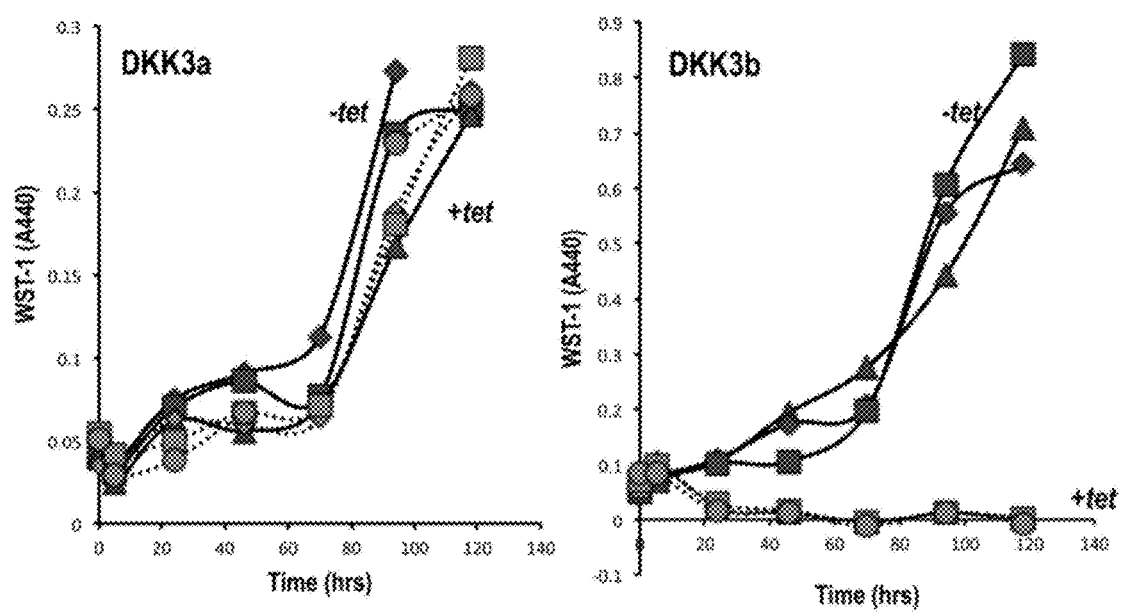
FIG. 2 depicts exemplary effects of DKK3a and DKK3b on PC3 cell proliferation. PC3 cell lines harboring the tet-regulated DKK3a or tet-regulated DKK3b were seeded into 96 well microtiter dishes. At the start of the experiment, replicate wells (n=5) were fed with growth medium±100 ng/ml tet and cell number was determined using the WST-1 reagent. Each data point represents the mean of quintuplets; 3 repeat time course experiments are shown.

To evaluate the tumor suppressor function of the two DKK3 gene products, DKK3a and DKK3b were cloned into the Tet-inducible, expression vector (pTRex) and transfected into PC3 prostate tumor cells that constitutively express the Tet repressor protein. The data in FIG. 2 show that DKK3a does not slow cell growth. On the other hand, DKK3b completely arrests cell proliferation, and leads to the loss of PC3 cells at later time points. These data illustrate that DKK3a lacks the tumor suppressor function associated with its intracellular form, DKK3b.

Figure 3:
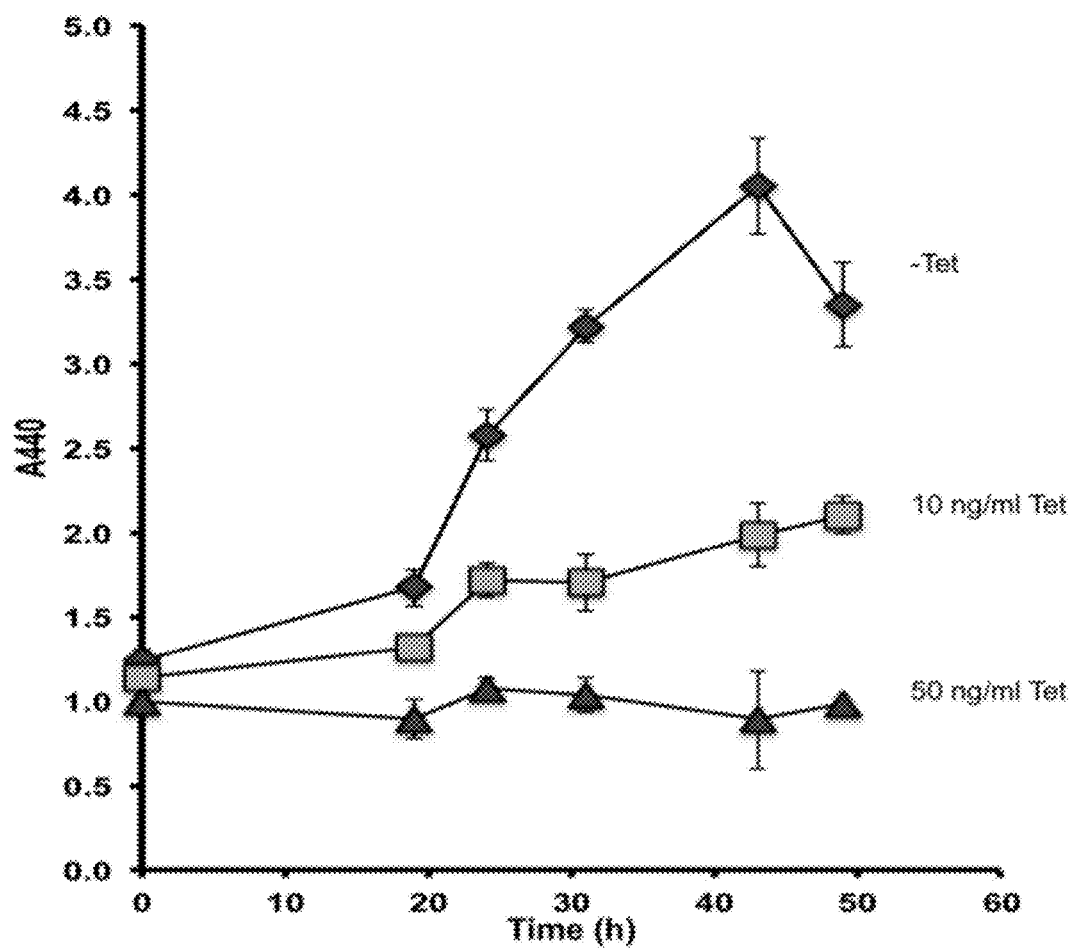
FIG. 3 depicts exemplary effects of increasing DKK3b on cell proliferation in Du145 cells. DU145 cells carrying the tet-inducible DKK3b were seeded into 96 well microtiter dishes. At t=0 tet was added as indicated and cell proliferation was measured using WST-1. Data are means, n=5.

Characterization of the Molecular Events Mediating DKK3b-Dependent Growth Arrest The ability of DKK3b to arrest cancer cell proliferation could be due to specific cell cycle arrest, enhanced apoptosis, and/or induced cell senescence. To explore these cellular event(s) without the confounding impact of aneuploidy/polyploidy and the genetic instability that are inherent in tumor cell lines, initial studies are done in immortal C8 astrocytes. These cells have a stable 2N gene copy number and show all of the properties of a primary astrocyte. They are easily transfected and have marginal native DKK3b. Epitope-tagged DKK3b are re-expressed in C8 cells using the tetracycline (tet)-inducible pTRex expression system that can be titrated to generate cells harboring increasing quantities of the tumor suppressor as illustrated in DU145 cells in FIG. 3.

Figure 4:
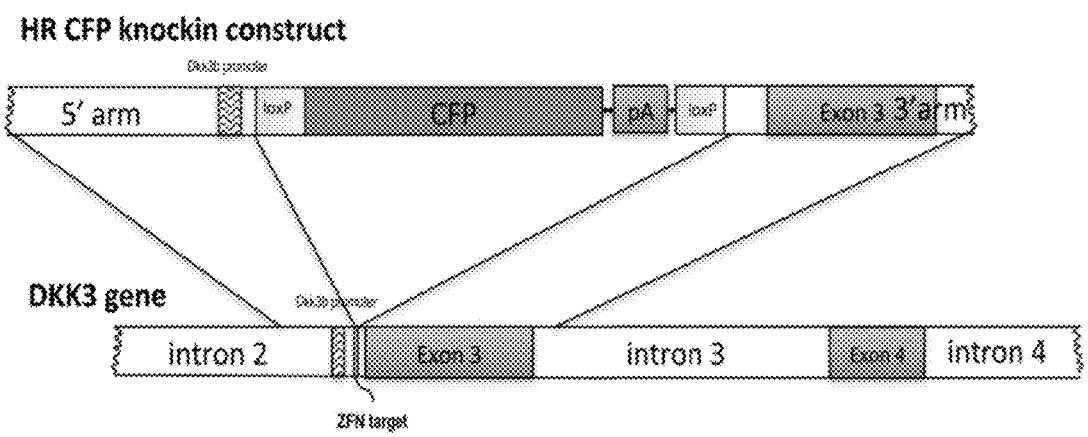
FIG. 4 depicts exemplary gene editing scheme for the Dkk3b promoter.

Since we propose that one of the primary actions of DKK3b is initiated by stopping the nuclear import of β-catenin, a TCF-driven TOPFlash luciferase reporter are used to monitor β-catenin dependent gene expression. MnuMG Wnt-dependent breast cancer cells were transfected with DKK3a and DKK3b and the TCF-driven luciferase (pTOPFlash), and the effects of the two DKK3 gene products on basal and Wnt7a stimulated reporter activity determined. As shown in FIG. 4, Wnt stimulation resulted in a 10-14 fold increase in TOPFlash signaling in the absence of any DKK3 or in the presence of the inactive DKK3a. Expression of DKK3b decreased TOPFlash signaling to near basal levels. These data illustrate the specific ability of DKK3b to silence β-catenin signaling, a central thesis of the molecular basis for the action of this tumor suppressor.

To confirm the direct interactions between βTrCP and DKK3b, RNAi-mediated knockdown of βTrCP in C8 pTOPFlash reporter cells is used to explore the impact of altered βTrCP expression on the ability of DKK3b to suppress TCF-reporter expression. Controls include the scrambled RNAi pools and/or off-target shRNAi lentivirus and the efficiency of knockdown are measured by immunoblot and immunocytochemistry. The loss of βTrCP will eliminate the DKK3b-dependent suppression of TCF-TOPflash reporter activity.

Based on these initial studies, the influence of Dkk3 derived gene products on cell proliferation and the cell cycle are examined in LNCaP, PC3 and DU145 cells using the tet-inducible DKK3a and DKK3b constructs. Cell proliferation (WST-1), viable cell counting, and cell cycle analysis using fluorescent activated cell sorting (FACS) of BrdU/7-AAD labeled cells are done. As shown in Table 1, DKK3b arrests the human prostate cancer PC3 cell at the G0/G1 phase of the cell cycle, while DKK3a had no effect on the cell cycle or on cell proliferation (also see FIG. 2).

TABLE 1

Effects of DKK3a and DKK3b on cell cycle in PC3 cells

| | Cell Cycle Analysis (% total cells) | | |
|---|---|---|---|
| | G0/G1 | S | G2/M |
| control | 44.1 | 27.2 | 17.1 |
| DKK3a | 42.3 | 28.5 | 16.3 |
| DKK3b | 95.7 | 2.6 | 1.2 |

Because DKK3b led to both growth arrest and loss of PC3 cells (FIG. 2), the impact of DKK3b on apoptosis is evaluated using flow cytometry, TUNEL assays, caspase-3 analysis and annexin V staining. TUNEL, caspase-3 measurements, and cell proliferation using Ki67 are repeated using standard immunocytochemical approaches to provide confirmation of the effects of DKK3b on apoptosis determined by flow analysis.

Once these basic functional parameters are established, the role of the DKK3b:βTrCP complex in tumor cell growth arrest are examined using the RNAi knockdown of βTrCP strategy detailed above for C8 cells. Loss of βTrCP in cancer cells will thwart DKK3b-induced growth arrest. The results of these studies will establish the role of DKK3b:βTrCP complex in modulating the β-catenin proliferation signal. DKK3b may affect more than one cellular pathway; however, focusing on the specific characterization of the inhibitory role of a DKK3b:βTrCP complex on cell growth provides a clear link between the well-known impact of β-catenin on cell proliferation and the tumor suppressor function of DKK3b.

Identification of DKK3b Modulated Signaling Pathway(s)

We propose that the DKK3b:βTrCP complex suppresses TCF-driven gene expression by preventing β-catenin from reaching its nuclear TCF target. Thus, analysis of the more than 50 known TCF-driven genes provides a well-defined end point to evaluate the efficacy of the DKK3b:βTrCP complex. (Willert, et al. 2002 *BMC developmental biology* 2:8.) RNA-seq provides an unbiased approach that allows transcriptome analysis of the whole set of TCF target genes. This contemporary genomics methodology provides a data set that not only allows the known TCF-driven genes to be evaluated, but can also be mined for unanticipated DKK3b dependent changes in the transcriptome. RNA-seq is a significantly more cost-effective and a less biased approach than commercially available PCR based array sets when cost/data point is considered. To determine the impact of DKK3b on TCF-driven gene expression, RNA-seq is used to define the impact of the inhibitory DKK3b:βTrCP complex on expression of a known cohort of ~110 TCF-driven gene targets.

From the RNA-seq analyses, 10-15 gene products are selected and used to assemble a DKK3b signaling array (DKK3b Response Array, DK3RA) to reliably report DKK3b function in prostate and breast cancer cells. Changes in the cellular content of these target protein(s) are confirmed using multiplexed, Millipore EpiQuant luminex assays of whole cell lysates, immunoblot analysis or immunocytochemistry. These studies are designed to demonstrate that the DKK3b tumor suppressor inhibits β-catenin signaling and provides a validated set of DKK3b altered transcripts (DK3RA) that can be used to monitor tumor suppressor function. Additionally, an invaluable data repository of DKK3b altered transcripts that can be mined for novel signaling partners will be generated and archived.

The Role of DKK3b:βTrCP Interactions on the Subcellular Redistribution of β-Catenin Over-expression of DKK3b can initiate the redistribution of β-catenin from the cytoplasm to the cell membrane without altering total β-catenin levels. (Hoang, et al. 2004 *Cancer Res* 64 (8):2734-2739.) Coupled with the finding that an intracellular DKK3b:βTrCP complex binds unphosphorylated β-catenin and can lead to β-catenin degradation, it is likely that the DKK3b:βTrCP complex performs at least three roles: 1) β-catenin sequestration; 2) β-catenin relocation; and 3) β-catenin degradation. Since these roles are likely to be temporally related, we use confocal, total internal reflectance fluorescence (TIRF) microscopy and real-time digital imaging to define the dynamics of subcellular redistribution of β-catenin, DKK3b and βTrCP in C8 cells and in our cancer cells lines expressing tet-induced, increasing concentrations of DKK3b. (Lee, et al. 2009 *Int J Cancer* 124 (2):287-297.) Our prior work detailing the dynamics of DKK3b trafficking guides our completion of these studies. (Farwell, et al. 1990 *J Biol Chem* 265 (30): 18546-18553; Stachelek, et al. 2000 *J Biol Chem* 275 (41):31701-31707; Stachelek, et al. 2001 *J Biol Chem* 276 (38):35652-35659.) In its simplest form, the membrane-bound DKK3b:βTrCP complex attracts unphosphorylated β-catenin leading to its membrane association. If adherens complexes are nearby this complex may deposit β-catenin in these attachment structures. (Hartsock, et al. 2008 *Biochim Biophys Acta* 1778 (3):660-669.) If not, the inactive complex may be degraded in the proteasome.

Characterization of the Organ/Tissue Distribution and Expression Profiles of DKK3b in the Mouse Little is known about the tissue distribution, developmental timing and/or the expression profile of DKK3b, and traditional immunocytochemical approaches are impractical because available antibodies recognize both DKK3b and DKK3a. To define the basic developmental timing and tissue distribution of DKK3b expression, we use the zinc-finger nuclease (ZFN)-based gene editing approach to produce a Dkk3b reporter mouse by redirecting the DKK3b promoter to drive expression of a fluorescent reporter (FIG. 4). (Clark, et al. 2011 *Zebrafish* 8 (3):147-149; Collin, et al. 2011 *Stem Cells* 29 (7):1021-1033; Kim, et al. 2009 *Genome research* 19 (7):1279-1288.) During validation of the ZFN pairs, gene-edited, Dkk3b-promoter driven CFP C8 ($C8^{Dkk3bCFP}$) cells are generated by default that are a valuable cell based reporter for high-throughput screening of combinatorial libraries.

Systematic functional analysis of the Dkk3b promoter is performed using CFP expression as the endpoint and in silico analysis (TranFac, Genomatrix algorithms) is used to identify individual Dkk3b promoter elements. This promoter survey approach will identify one or more promoter modulators that modulate transcription from this locus.

The Dkk3b reporter mouse provides two important in vivo models. 1) Heterozygotes ($Dkk3b^{+/CFP}$) express all three gene products from the Dkk3 locus, DKK3a, DKK3b and CFP. These mice are used in define the developmental timing and tissue distribution of DKK3b in embryos, neonates and adults. DKK3b promoter driven CFP is expected to show widespread distribution in tissues. 2) Homozygotes ($Dkk3b^{CFP/CFP}$) are functional knockouts that express DKK3a, but not DKK3b, because the Dkk3b-promoter of both alleles has been diverted to drive CFP expression. These Dkk3b "knockout" mice, unlike the original Dkk3a knockout, lose the DKK3b tumor suppressor and are expected to show markedly increased cancer risk and potential developmental abnormalities.

Methods and Procedures

Biological Assays for Cell Proliferation, Cell Cycle, Apoptosis and Senescence Cell proliferation is monitored using the WST-1 reagent according to manufacturer's instructions. Cell proliferation, cell cycle analysis, and apoptosis are conducted using FACS analysis of BrdU tagged cells that are post labeled with fluorescent antibodies directed against epitope-tagged DKK3b and Annexin V (apoptosis). Alternatively, apoptosis are followed by TUNEL assays according to established methods in the laboratory. Cell senescence is determined by β-galactosidase activity using commercially available kits. All analyses are done in triplicate and repeated at least three times to validate the data.

DKK3 cDNA Constructs, Plasmid, Viral Expression Constructs and Immunological Probes Gateway® technology (Invitrogen) is used to generate entry plasmids harboring epitope tagged DKK3a and DKK3b. This shuttle vector system permits the rapid assembly of a wide repertoire of plasmid or viral expression vectors by λ phage-based recombination. Both constitutive and tet-inducible destination vectors are used in the laboratory. Gateway® technology is also available to shuttle PCR generated shRNAi into cells or tissues. A complete collection of retroviral and lentiviral based shRNAi human and mouse libraries are available.

Deep Sequencing of DKK3b Altered RNA Libraries

Cells harboring tet-inducible DKK3a or DKK3b are exposed to tetracycline and grown for up to 24 h. Total RNA are isolated by Qiagen RNeasy columns and poly A+ mRNA isolated by oligo-dT purification. Triplicate mRNA-seq libraries from control (no tet), DKK3a and DKK3b expressing cells are made using commercially available kits.

Gene Editing of the Dkk3b Promoter Locus

Dkk3b promoter targeted ZFN pair selection is guided by methods developed by Wolfe. (Wolfe, et al. 2003 *Biochemistry* 42 (46):13401-13409; Meng, et al. 2008 *Nature biotechnology* 26 (6):695-701; Zhu, et al. 2011 *Development* 138 (20):4555-4564.) cDNAs encoding target ZFN pairs are synthesized de novo and cloned into the pCS-FokI vector. ZFN target modification is done in the isogenic C8 cell line and target specificity evaluated using PCR. Validation of ZFN target modification are done by Cel-1 assays, by single-stranded oligo homologous recombination (HR) repair and by HR-mediated insertion of a floxed CFP reporter. (Chen, et al. 2011 *Nature methods* 8 (9):753-755.) Off-target ZFN activity are evaluated in silico and the top 3 off-target sites interrogated by PCR analysis. Validated ZFN pair(s) that edit the target region of the Dkk3b promoter and the HR based CFP-pA cDNA construct are used to make Dkk3b reporter mice.

In vitro synthesized ZFN mRNAs and the Dkk3b-promoter targeted HR-pLox-CFP-pA-pLox repair cDNA are injected into 50-75 fertilized C57BL/6 mouse oocytes in the Transgenic Animal Modeling Core at UMMS. Single cell embryos are implanted into surrogates and offspring are genotyped using Dkk3b-promoter specific PCR. Dkk3b-promoter gene edited mice are expanded into two colonies: $Dkk3b^{+/CFP}$ heterozygotes are bred for use in developmental and tissue distribution studies, and $Dkk3b^{CFP/CFP}$ homozygotes are bred for evaluation of tumor susceptibility of the Dkk3b knockout mouse. If the loss of Dkk3b proves lethal, the basis for lethality is then determined and the tissue-specific Cre expression is used to excise the CFP reporter and restore Dkk3b expression in the tissue(s) required for survival.

With identification and characterization of the impact of a DKK3b:βTrCP complex on the biology of β-catenin signaling and the tumor suppressor function of DKK3b, the ability of DKK3b to "sequester" β-catenin, arrest tumor cell growth and block TCF-driven proliferation/survival signals provides a straightforward mechanism for tumor suppressor function. The unbiased, RNA-seq, bioinformatics-based approach is used to identify the affected target gene pathways. From these data, a validated set of DKK3b reporter genes will be selected (DK3RA) and used to monitor DKK3b function. Analysis of the dynamics of DKK3b-induced shuttling of β-catenin between different intracellular compartments is a straightforward cell biology problem that is approached by static and dynamic imaging paradigms. These data provide basic information on what steps in the process can be targeted for therapeutic intervention.

Additionally, generation of the DKK3b$^{+/CFP}$ reporter cell line and DKK3b$^{+/CFP}$ mouse models are invaluable for the study of tumorigenesis. Contemporary gene editing strategies using ZFN technology significantly reduce the time required to develop testable biological models. The C8$^{Dkk3bCFP}$ cells generated during the validation process provide a significant value-added benefit—they are useful to explore methods of Dkk3b promoter activation and for the discovery of small molecules that alter DKK3b expression. Production of the Dkk3b reporter mouse is significantly more cost effective than traditional ES cell based homologous recombination strategies and decrease the time to generate a viable mouse model by >80%. Characterization of Dkk3b promoter function can be directly applied to in vivo intervention of the oncogenic process and to develop novel therapeutic approaches to cancer.

Mechanistic Analysis of DKK3b-Induced JNK Activation in Prostate Tumors

The JNK pathway is widely recognized as an important regulator of tumor biology and serves as a key cellular defense mechanism to prevent genetic instability and the development of aneuploidy. (Kennedy, et al. 2003 Cell Cycle 2 (3):199-201; Vivanco, et al. 2007 Cancer Cell 11 (6):555-569; Whitmarsh, et al. 2007 Oncogene 26 (22):3172-3184; MacCorkle, et al. 2004 J Biol Chem 279 (38):40112-40121; Miyamoto-Yamasaki, et al. 2007 Cell Biol Int.; 31 (12): 1501-1506; Nakaya, et al. 2009 Cell Biochem Funct 27 (7):468-472; Wang, et al. 2009 J Pathol 218 (1):95-103.) Previous reports have shown that DKK3 over-expression in tumor cells increases JNK activity leading to inhibition of cell proliferation and increased cell loss mediated, in part, by apoptosis. (Edamura, et al. 2007 Cancer Gene Ther 14 (9):765-772; Abarzua, et al. 2005 Cancer Res 65 (21):9617-9622; Ikezoe, et al. 2004 Br J Cancer 90 (10):2017-2024; Kawano, et al. 2006 Oncogene 25 (49):6528-6537.)

Figure 5:
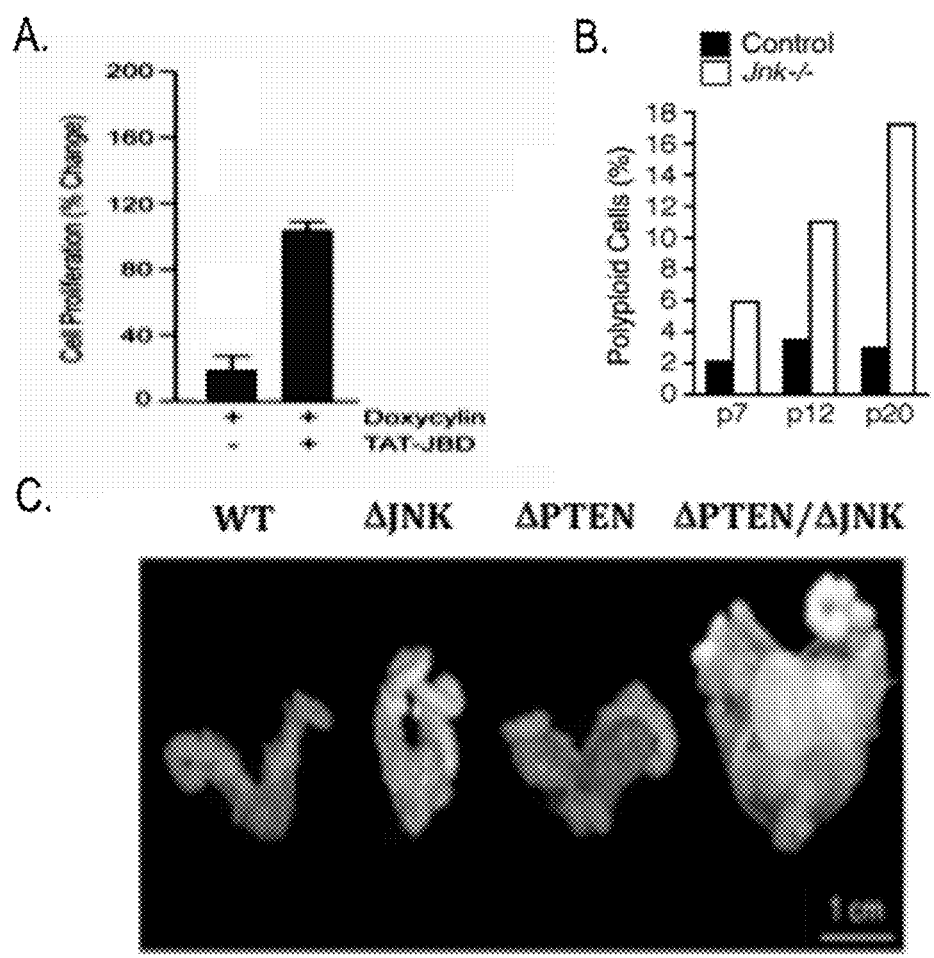
FIG. 5 depicts exemplary, A. Effect of JNK inhibition on DKK3b-induced cell loss; B. Ploidy analysis in control and ΔJnk MEF; and, C. gross morphology of prostate tumors in wildtype, ΔJnk, ΔPten and ΔPten/ΔJnk mice. A. DU145 cells expressing DKK3b were treated without or with the JNK inhibitor TAT-JBD for 48 h. Cell proliferation determined as in FIG. 2. B. Data from FACS with >30,000 PI-stained cells gated on >4 n cells; p=passage number. C. Prostates collected at 20 weeks of life.

In our hands, DKK3b-dependent growth arrest in DU145 prostate tumor cell requires, in part, the JNK stress kinase pathway (FIG. 5A). While DKK3b halted cell proliferation, TAT-JBD inhibition of JNK activity blocked cell loss (FIG. 5A), suggesting that the JNK pathway is required for cell loss. These results agree with our observations that Jnk inhibits prostate tumor formation in the well-established conditional Pten mouse model of prostate cancer. PTEN (phosphatase and Tensin homology) is a tumor suppressor commonly mutated in cancer that recently was shown to have a direct role in preventing chromosomal instability: ΔPten/ΔJnk mice lack PTEN and JNK in prostate epithelium and develop more aggressive cancer than animals lacking PTEN alone (ΔPten) (FIG. 5C). (Baker 2007 Cell 128 (1):25-28; Blanco-Aparicio, et al. 2007 Carcinogenesis 28 (7):1379-1386; Trotman, et al. 2007 Cell 128 (1):141-156; Yin, et al. 2008 Oncogene 27 (41):5443-5453; Shen, et al. 2007 Cell 128 (1):157-170; Puc, et al. 2005 Cancer Cell; 7 (2):193-204; Wang, et al. 2003 Cancer Cell 4 (3):209-221.) While this result clearly illustrates the role for the JNK pathway in preventing this cancer, the biological processes that JNK regulates remain unclear. Control of genetic instability represents a likely mechanism for JNK function to prevent cancer. Preliminary studies using murine embryonic fibroblasts (MEF) show that loss of JNK expression dramatically increases chromosomal instability and led to aneuploidy (FIG. 5B).

The increased genetic instability resulting from the loss of JNK is responsible for the more aggressive tumors in prostate epithelium (FIG. 5C). We propose that DKK3b inhibits tumor growth, in part, by a JNK-dependent manner in vivo. The invention provides the first mechanistic framework for understanding how the DKK3b-JNK signaling axis prevents tumorigenesis and thus significantly advances our understanding of the role of this kinase pathway in human cancer.

Thus, the invention demonstrates a role for JNK in preventing the genetic instability that promotes tumor formation and defines the molecular connections between DKK3b and the JNK pathway.

Characterization of the DKK3b-JNK Signaling Axis in Prostate Cancer

Expression of DKK3 is lost in most prostate tumors, and DKK3b is the biologically relevant tumor suppressor from the Dkk3 locus. The JNK activating kinase Mkk4 is also mutated in a subset of primary human prostate tumors. (Whitmarsh, et al. 2007 Oncogene 26 (22):3172-3184; Kim, et al. 2001 Cancer Res; 61 (7):2833-2837; Taylor, et al. 2008 Cancer Lett 272 (1):12-22.) However, it is unknown if loss of both gene products synergize to generate a more severe cancer. The invention establishes correlative and causative connections between DKK3b and the JNK pathway that demonstrate the importance of this signaling axis in preventing prostate cancer. Primary human prostate tumor samples representing a range of Gleason scores for expression of DKK3b, DKK3a, β-catenin, MKK4, MKK7 and JNK and phospho-analogs are screened by immunocytochemistry, qPCR, and immunoblot analysis. Expression of the tumor suppressor PTEN is also screened to determine if the connections between the DKK3b and JNK pathways require Pten mutations. We propose that tumor severity is inversely related to DKK3b levels and directly related to β-catenin nuclear localization, and the expression or activity of JNK, MKK4 and/or MKK7 is expected to be inversely correlated with tumor severity.

Analysis of Genetic Instability in Prostate Epithelium

Genetic instability is associated with DNA breaks, translocations and the development of aneuploidy. The degree of genetic instability is determined in tissue sections of prostates from ΔPten and ΔPten/ΔJnk mice collected at several stages of tumor development including when only PIN lesions are evident. The enhanced prostate tumorigenesis in ΔPten/ΔJnk mice indicates that regulatory mechanisms that prevent uncontrolled cell growth (such as apoptosis or senescence) are defective due to loss of JNK. Loss of these pathways disconnects the DKK3b tumor suppressor from the genomic surveillance machinery and ultimately leads to more aggressive tumor formation.

Tumor Inhibition Using Lentivirus Delivery of Activated JNK or DKK3b

The idea is tested that prostate-specific expression of DKK3b or activated JNK inhibits PIN formation and tumor growth in murine models of prostate cancer. For these studies, murine models are modified to include a prostate-specific luciferase reporter to visualize tumor growth in living mice. Lentiviral delivery system is used to express DKK3b and/or a constitutively active version of JNK specifically under the control of the prostate-specific probasin promoter. (Vivanco, et al. 2007 *Cancer Cell* 11 (6):555-569.) The effect of prostate-specific expression of DKK3b or active JNK on tumor growth is monitored over time in live animals by evaluating expression of the luciferase reporter.

Dependence of JNK for Anti-Tumor Effects of DKK3b

Although DKK3b blocks cancer cell proliferation ex vivo, through a mechanism that involves JNK, it is unknown if this holds true in vivo. Gene replacement by lentiviral constructs will be used to express both DKK3b and TAT-JBD—a specific peptide inhibitor of JNK—in prostate tumors of ΔPten/Luciferase reporter mice. The effect of JNK inhibition on DKK3b function is evaluated by analyzing PIN formation in sections of prostates from sacrificed mice and monitoring tumor regression over time in live animals. We expect that loss of JNK activity will lead to more PIN formation.

Molecular Mechanism(s) of JNK Activation by DKK3b

The activation of upstream kinases known to lead to JNK phosphorylation is examined. The RNA-Seq data set is queried to identify changes in gene expression affecting pathways known to regulate JNK signaling. Multiplex ELISA is used to analyze changes in cytokine expression profiles that could lead to JNK activation. The salient findings from our in vitro analysis are confirmed in vivo using gene replacement/RNAi knockdown of candidate pathway members suspected of playing a role in tumor regression and/or suppression of PIN formation. For example, identification in vitro of a DKK3b-altered MAP-KKK or DKK3b-dependent production of JNK-activating cytokine(s) will be experimentally evaluated in tumors expressing DKK3b.

Methods and Procedures

Laser Scanning Cytometry

Laser scanning cytometry is used to analyze ploidy changes in prostate tumor cells from ΔPten and ΔPten/ΔJnk mice. Because this method uses sections of intact prostate, tissue architecture is preserved allowing for the assessment of PIN formation. Prostate tissue sections are stained with antibodies to E-cadherin (to mark stromal cells), N-cadherin/cadherin-11 (to mark tumor cells) and propidium iodide to label DNA followed by analysis using laser scanning cytometry. Analysis of DNA content in stromal cells (positive for E-cadherin but negative for N-cadherin and cadherin-11) serves as an internal control for the diploid cell population. The DNA content of tumor cells (positive for N-cadherin and cadherin-11 and low levels of E-cadherin) is compared to stromal cells to determine ploidy changes. Control experiments include prostates from wild type, Pb-Cre, Pten$^{f/f}$ and Jnk1$^{f/f}$/Jnk2$^{-/-}$ mice.

Morphological Methods

Standard immunohistochemical and immunofluorescent techniques is used to analyze prostate tissue morphology and the presence of DNA strand breaks in ΔPten/ΔJnk mice. Prostate tissue sections are stained with hematoxylin and eosin to reveal morphology. DNA strand breaks is assessed using antibodies to phospho-H2Ax and p53BP. Chromosomal rearrangements are evaluated using the spectral karyotyping (SKY) technique. Cellular senescence is determined by assaying the senescence marker β-galactosidase. Apoptosis is evaluated by assessing the levels of nicked DNA using the (TUNEL) assay and caspase-3 activity. Proliferation is quantified using Ki67 or BrdU immunostaining. Prostate tissue from wild type, Pb-Cre, Pten$^{f/f}$ and Jnk1$^{f/f}$/Jnk2$^{-/-}$ mice serve as controls. Tumor sections will be evaluated using confocal microscopy and fluorescent images analyzed for statistical differences using Image Pro Plus® software.

Analysis of Human Prostate Tumor Gene Expression

Tumor specimens are obtained from the UMMS Tissue Bank and represent various grades of tumor severity based on Gleason scores. RNA is isolated from tumor samples and screened for expression of DKK3b, DKK3a, β-catenin, Pten, Mkk4, Mkk7 and Jnk using qPCR assays and results confirmed using immunoblot and/or immunocytochemistry to detect protein expression. These experiments establish, for the first time, a correlative connection between DKK3b, the JNK pathway, and prostate cancer severity. We expect an increasing Gleason score to be positively correlated to the loss of both Dkk3b and Mkk4 geneexpression. Alternatively, mutational inactivation could functionally suppress DKK3b and MKK4 activities. Therefore, the Dkk3 and Mkk4/7 genes are sequenced to identify possible inactivating mutations that do not affect overall expression.

Mouse Models of Prostate Cancer

Our novel murine models of prostate cancer are crossed to a prostate specific luciferase reporter mouse strain and the progeny are used for these studies. Prostate specific luciferase expression is directed by a transgene that expresses the firefly luciferase gene under the control of a probasin promoter modified to include two androgen response elements (ARR2-Pb-Lux, (Ellwood-Yen, et al. 2006 *Cancer Res* 66 (21):10513-10516), hereafter as Lux). Lux reporter mice are crossed to our conditional mice that lack expression of PTEN (ΔPten) or PTEN and JNK (ΔPten/ΔJnk) in the prostate, generating both Lux-ΔPten and Lux-ΔPten/ΔJnk strains for live animal imaging studies.

Construction and Use of Prostate-Specific, Lentiviral Delivery System

Lentiviral constructs for prostate-specific expression of JNK, constitutively active JNK (a fusion between the upstream JNK activator MKK7 and JNK, MKK7-JNK), a specific JNK inhibitor TAT-JBD (a fusion protein of the JNK Binding Domain (JBD) of the JIP1 scaffolding protein appended to the HIV TAT sequence) and DKK3b are constructed as detailed herein. Expression of all constructs is driven by the ARR2-Pb promoter to ensure prostate specific expression and include an epitope tag to facilitate detection of expressed proteins. Lentiviral supernatants are administered to live animals either by tail vein injection or alternatively, by direct intratumoral injection. Preliminary control experiments using wild-type mice are done to optimize the percentage of prostate cells infected through either mode of injection using immunofluorescent microscopic analysis of prostate sections stained with epitope specific antibodies.

Quantitation of Tumor Growth in Live Animals

The Lux-ΔPten and Lux-ΔPten/ΔJnk mouse strains develop prostate tumors that express the firefly luciferase reporter gene, allowing us to monitor tumorigenesis in live animals. Sedated mice are injected with the luciferase substrate, luciferin, and emitted light are measured using the Xenogen® IVIS imaging system. Both early stage primary lesions and metastases that have spread to other organs can be visualized using this system. Wild type Pb-Lux mice that lack tumors are used as negative controls. Specific gene replaced mice (DKK3b, MKK7-JNK and TAT-JBD) are imaged before viral infection to establish a baseline for tumor size. Subsequent images are collected weekly for 4 weeks to determine the effect(s) of modulation of the DKK3b and JNK pathways on tumor growth. Initial control studies are done to optimize the time between luciferin injections and live animal imaging. Additional control studies include injection of an empty lentiviral construct.

Lentivirus Production and Delivery

Production and validation of concentrated lentiviral supernatants are done using standard protocols established in our laboratories. Viral titers are determined by limiting dilution and expression of the specific epitope-tagged proteins will be determined by immunofluorescence techniques. Administration of lentiviral particles are achieved by injection into the tail vein of mice twice over two days. Alternatively, direct delivery of lentiviral particles to the prostate of anesthetized mice are done through a small incision in the peritoneum in the lower abdomen. Approximately 10-20 μl of concentrated lentiviral stock (~108 particles) are injected into the prostate and the wound closed using surgical sutures. Surgical recovery of the animals is carefully monitored for signs of infection or other complications. Controls include animals injected with PBS or empty lentivirons.

Assessment of Prostatic Intraepithelial Neoplasia (PIN) Lesions

Standard histochemical and immunological staining techniques are employed to evaluate PIN lesion development in our murine models of prostate cancer. The prostate are harvested at time points spanning the onset of disease to the beginning of tumor formation. Serial sections of prostate tissue are prepared from paraffin-embedded or frozen tissue blocks. One section are stained with hematoxylin and eosin to identify the morphological disruptions that characterize PIN lesions and adjacent sections are used for immunological detection of lentiviral-delivered gene products using epitope tagged antibodies. The total number of PIN lesions and the percentage of PIN lesions (if any) that express lentiviral delivered gene construct(s) are determined from at least five mice at every time point.

Endpoint Analysis of Prostate Tissue

For all experiments involving mice, prostate tissue are harvested at the time of animal sacrifice. Paraformaldehyde-fixed prostate tissue is processed to generate paraffin and frozen tissue sections for analysis of PIN lesions, lentiviral-mediated gene expression and luciferase activity. Unfixed prostate tissue from additional mice is used for transcript analysis using qPCR and for determination of protein expression by either immunoblotting or multiplexed ELISA (luminex) assays. The small size of prostates in mice that serves as negative controls are in early stages of disease require pooled tissue to generate enough material for all analyses.

Statistics and Power Analysis

The number of mice in each group is determined by the statistical power required to detect significant, biologically relevant differences. A meaningful difference in means between groups can be detected using t-test assuming normality. The difference in means is expressed in units of standard deviation (which accounts for the magnitude of inter-animal variability). With 8-10 mice in each group, differences can be detected between means that are greater than 1.25 SD (since smaller differences will not likely be biologically relevant) at a 0.05 significance level. We anticipate that increased Dkk3b expression will result in statistically significant tumor growth delay.

Most established tumors regardless of tissue origin show evidence of genetic instability. While it is likely that tumors from ΔPten/ΔJnk mice are genetically unstable, it is the analysis of the earliest events in tumorigenesis—the formation of PIN lesions—that prove fruitful regarding cause and effect. To overcome analytical limitations due to the small size of early PIN lesions, we use laser scanning cytometry. A primary advantage of laser scanning cytometry is the retention of tissue architecture allowing for the identification of PIN lesions based on morphology rather than tumor antigen(s) expression. This approach also overcomes the caveat that differences in cadherin expression may not occur in early PIN lesions and/or that differential cadherin expression may require JNK-dependent AP-1-mediated transcription. Because tissue architecture is preserved in laser scanning cytometry, other criteria such as androgen receptor (AR) expression can be used to identify PIN lesions: normal prostate tissue shows a well-defined expression of AR in a single layer of epithelial cells, whereas PIN lesions show disorganized, multi-layer AR expression.

Analyzing DNA strand breaks in early PIN lesions as well as late stage tumors using immunocytochemisty and SKY, respectively, allows us to connect increased DNA damage in PIN lesions to increased chromosomal translocations in late-stage tumors. While it is possible that we will not find differences in genetic instability between ΔPten and ΔPten/ΔJnk tumors on a per cell basis, the data obtained will provide valuable information because the frequency of appearance rather than the degree of instability in affected cells may be the driving force that leads to increased prostate tumor formation in ΔPten/ΔJnk animals. Such a result highlights the role of the JNK pathway in maintaining genetic integrity.

Another potential concern is that limitations/defects in upstream activators of JNK may prevent increased JNK expression from affecting tumor growth. To address this, we use the lentiviral delivery system to express a constitutively active MKK7-JNK fusion protein that bypasses the need for upstream activating kinases. This serves an important proof-of-concept test of our hypothesis that increasing JNK activity levels inhibits tumor growth, and sets the stage for additional experiments that seek to increase endogenous JNK activity in tumors by modulating the JNK pathway.

While we propose that DKK3b blocks cancer cell growth, in part, through a JNK-dependent process, it is just as possible that DKK3b also works through JNK-independent mechanisms to inhibit cancer cell growth. This possibility can be tested by expressing DKK3B in tumors of ΔPten/ΔJnk mice. If no change in tumor status occurs, then the protective function of DKK3b requires JNK. Alternatively, DKK3b may induce a partial inhibition of tumor growth in the absence of JNK suggesting the existence of alternative JNK-independent pathways that control tumor growth.

Finally, Lentiviral-mediated delivery of DKK3b and JNK to prostate tissue presents potential concerns. If tail vein delivery of lentiviral particles does not attain levels of infection necessary to affect tumor growth using of virus, uninfected tumor cells will continue to proliferate and could, if present in sufficient numbers, mask any growth inhibition offered by DKK3b/JNK. This pitfall is of particular concern for experiments designed to regress established tumors. To address this problem, pilot studies are performed using a GFP reporter virus to determine if tail vein injection yields sufficient prostate infection rates. If tail vein injection of viral particles proves inefficient, viral particles are injected directly into the prostate of anesthetized mice through a small incision made in the abdomen. Initial control studies will determine volume/concentration of viral particles and the degree of expression of exogenous proteins. Mice injected with PBS and empty lentiviral particles are run in parallel as additional controls for these experiments.

Relationship Between DKK3b and Triple Negative Breast Tumor Phenotypes

Figure 7:
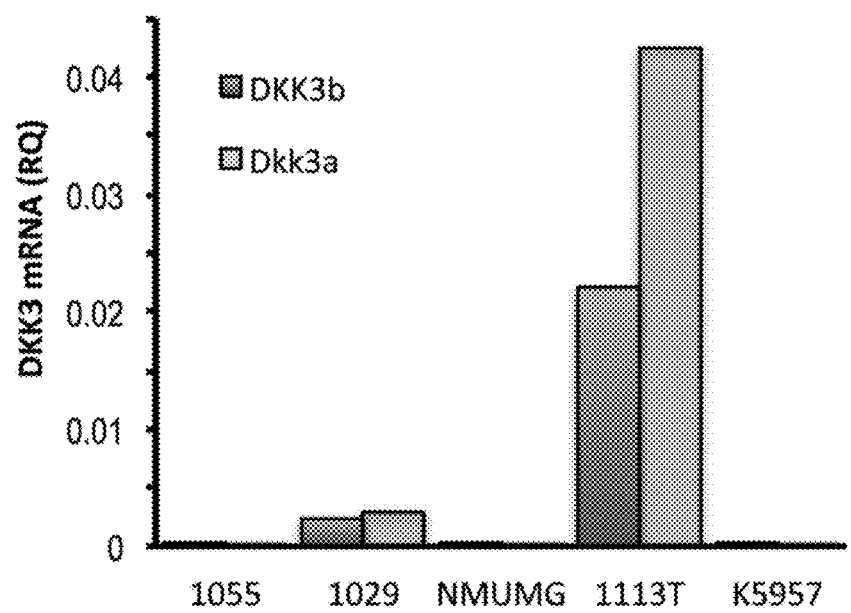
FIG. 7 depicts exemplary Dkk3b shows variable expression among mouse tumor-derived cell lines. Cell lines 1055, 1029, 1113T and K5957 were derived from primary tumors of the TBP knockout mouse. NMuMG are immortalized normal mammary epithelium.

Like other epithelial cancers, DKK3b expression is altered in the mammary tumors in our mouse model (FIG. 6), and shows a cell specific, inverse relationship with cytoplasmic β-catenin. This heterogeneity of DKK3b and β-catenin expression was maintained in tumor-derived cell lines indicating that different cohorts of tumor resident cells can be isolated and their molecular defect(s) characterized ex vivo (FIG. 7).

Loss of DKK3b may play an important role in the formation and maintenance of so-called "triple negative" breast cancers (TNBC). ER, PR, Her2 triple-negative breast cancers are a class of aggressive tumors with few, if any, options for treatment. To examine this, two mouse models are employed to explore the evolution of these tumors and the molecular details that contribute to their aggressive nature. The first is our novel mouse model (TBP) that mimics TNBC due to the loss of three critical tumor suppressor pathways: Rb; BRCA1; and p53 that are affected in human TNBC. (Simin, et al. 2005 Cold Spring Harb Symp Quant Biol 70:283-290; Kumar, et al. 2012 PLoS Genet. 8 (11) e1003027; D'Amato, et al. 2011 PLoS One 7 (9) e45684; Herschkowitz, et al. 2007 Genome Biol 8 (5):R76.) Our global gene expression survey of 13 mouse models revealed that the TBP mouse mimicked human TNBC. The second model, MMTV-Wnt1, is a well-established model of breast cancer that also resembles TNBC, and was exploited to study tumor-initiating cells. We hypothesize that dysregulated Wnt activity contributes to the tumor phenotype, and targeting this pathway with DKK3b will block tumor progression, which will translate into significant clinical benefits for breast cancer patients.

Since DKK3b suppresses tumorigenesis, in part, by limiting the function of Wnt dependent tumor initiating cells and this is novel and significant. Our finding that DKK3b shows an inverse relationship with cytoplasmic β-catenin in mammary tumors is unprecedented and clearly shifts the therapeutic paradigm to how DKK3b functions to arrest tumor cell growth. Characterization of the anti-tumor properties of DKK3b offers a novel therapeutic target with the promise for development of an effective rational treatment of a lethal class of aggressive mammary tumors.

Evaluate the Contribution of DKK3b Expression to Mammary Tumorigenesis

The Wnt ligand is a potent morphogen and mitogen that fosters tumor progression and the malignancy of TBP tumors at multiple stages of development. The time course of both β-catenin and DKK3b expression are defined in tissue sections from mammary tumors, pulmonary metastases, and MINs (mammary intraepithelial neoplasias) of TBP and Wnt1 mice. Normal patterns of β-catenin and DKK3b expression are assessed in wild type control tissues. Tissue samples are examined using immunofluorescence, in situ hybridization, and multiplexed ELISA of isolated tumor resident cells.

Cell sorting paradigms are used to enrich specific subsets of the heterogeneous tumor population using the cell surface markers CD49f, CD24 and CD61 that label tumor-initiating cells. Alternatively, laser capture micro-dissection are used to isolate morphologically distinct cell populations from TNBC tumors. Cells are isolated by sorting or micro-dissection and characterized by qPCR, multiplexed ELISA, immunoblot, and the DK3RA assay. A minimum of 24 TBP and 24 Wnt1 tumors are systematically examined to establish the coincident or mutually exclusive expression of β-catenin and DKK3b. Our initial results showed high levels of DKK3b are associated with low levels of cytoplasmic β-catenin within a single cell. The clinical relevance of these tumor targets is corroborated by evaluating patient-derived specimens. Tumors are examined ranging in grade and clinical marker status, using sufficient numbers to establish statistically significant associations, as we have published previously (46-49) to define the phenotype(s) of different tumor resident cells in TNBC tumors.

Examine the Effects of Altered DKK3b on Mammary Tumor Initiation

Figure 8:
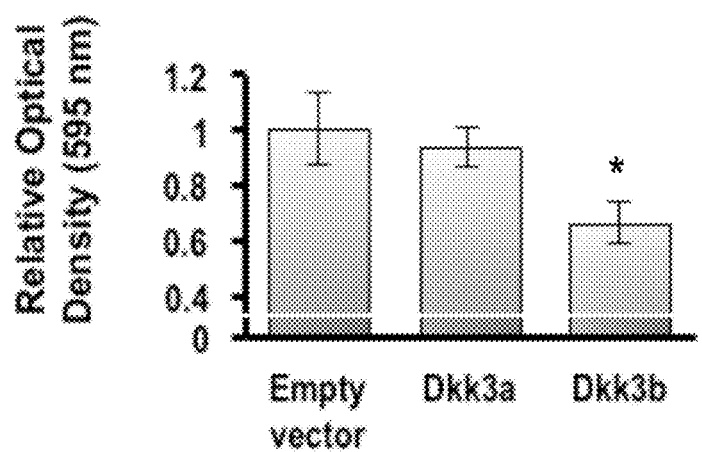
FIG. 8 depicts exemplary exogenous Dkk3b but not Dkk3a suppresses proliferation of immortalized NMuMG mouse mammary cells (p<0.002).

The effects of altered DKK3b expression on tumor initiation are determined using Wnt1-transformed, immortalized mouse mammary epithelial cells, NMuMG. DKK3a failed to alter proliferation of NMuMG cells, like PC3 and DU145 cells, while DKK3b slowed cell growth (FIG. 8). NMuMG cells expressing the tet-inducible DKK3b are transformed by Wnt1 and the effects of increasing DKK3b on Wnt1-dependent tumor initiation evaluated using soft agar cultures and tumorsphere formation assays.

NMuMG cells do not form tumors unless transformed by oncogenic signals such as the Wnt ligand. Orthotopic transplants of tet-inducible, DKK3b-expressing NMuMG cells in NOD/SCID mice undergo transformation and the effect(s) of DKK3b on tumorigenesis evaluated in vivo. Resulting tumors are harvested and DKK3b-dependent changes characterized by morphology (H&E), proliferation (Ki67), apoptosis (TUNEL), β-catenin distribution patterns (total cell and cytoplasmic/nuclear ratio) and LEF/TCF-regulated target genes, such as E-Cadherin, N-Cadherin, AXIN2, Cyclin D1 and c-Myc. Since tumor-initiating cells are enriched by Wnt1 stimulation, FACS (CD49f$^{high}$, CD24$^{low}$, CD61$^+$) are used to isolate and quantify tumor-initiating cell populations. (Cho, et al. 2008 Stem Cells 26 (2):364-371; Vaillant, et al. 2008 Cancer Res 68 (19):7711-7717.) We expect that increased levels of DKK3b will attenuate both tumor initiation and tumor maintenance.

Establish the Impact of Endogenous DKK3b on Wnt1-Induced Mammary Tumorigenesis In Vivo The conditional, loss-of-function Dkk3b$^{CFP/CFP}$ reporter mouse is mated with MMTV-Wnt1 mice (JAX). Importantly, the conditional deletion of Dkk3b can be reversed by co-expression of several mammary gland directed (MMTV-, BLG-, WAP-) Cre recombinases. Our hypothesis is that reduced DKK3b levels will aggravate Wnt1-induced tumor development due to the unchecked increase of cytoplasmic β-catenin. Tumor latency and tumor phenotypes of the parent Dkk3b$^{CFP/CFP}$ (Dkk3b knockout), MMTV-WNT1 (Dkk3b expressor), and crossed Dkk3b$^{CFP/CFP}$/MMTV-WNT1 (Dkk3b knockout, tumor producers) and Dkk3b$^{CFP/CFP}$/MMTV-WNT1/MMTV-Cre) (Dkk3b restoration, tumor producer) animals are compared. (Simin, et al. 2005 *Cold Spring Harb Symp Quant Biol* 70:283-290; Herschkowitz, et al. 2007 *Genome Biol* 8 (5):R76; Lu, et al. 2011 *Mol Cancer Res* 9 (4):430-439; Simin, et al. 2004 *PLoS Biol* 2 (2):E22.) In the simplest analysis, we anticipate mice lacking DKK3b to have more tumors with faster onset, and the Cre-repaired animals expressing DKK3b to have fewer tumors with slower onset.

Figure 9:
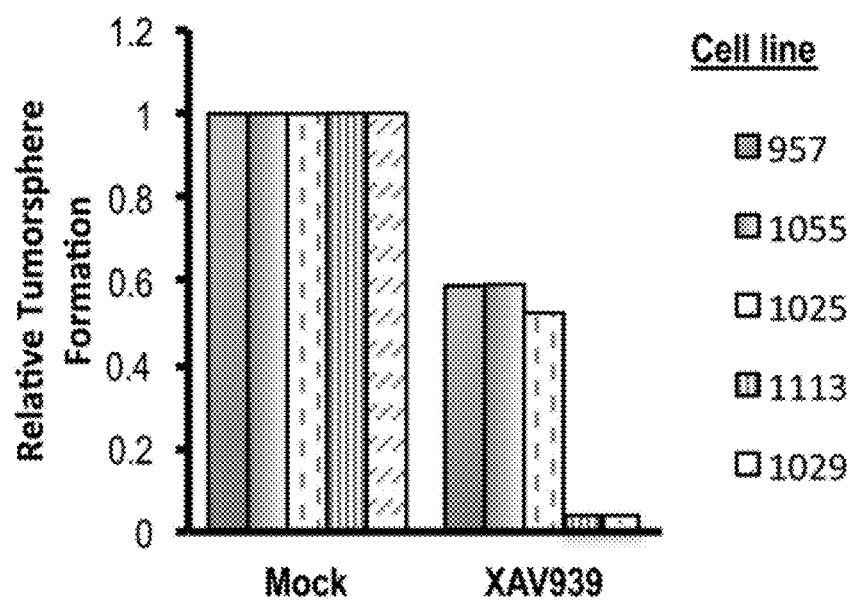
FIG. 9 depicts exemplary Wnt pathway inhibitor, XAV939, suppressed tumorsphere formation of five independent TBP tumor-derived cell lines, indicating the requirement of Wnt signaling.

Determine the Effects of Altered DKK3b on the Function of Mammary Tumor Initiating Cells Primary cells derived from mammary tumors in the TBP mouse with DKK3b$^{high}$ (MMTVWnt1: Dkk3b$^{+/CFP}$) and DKK3b$^{low}$ (MMTV-Wnt1:Dkk3b$^{CFP/CFP}$) expression patterns provide a unique resource to evaluate the effect of DKK3b activity on tumor-initiating cells. Using FACS sorted pools of high and low DKK3b expressing cells from primary tumors, the impact of DKK3b on tumor initiating capacities are examined by ex vivo and in vivo assays. We expect DKK3b high cells to suppress Wnt signaling at the level of its intracellular transducer, β-catenin, and thereby reduce tumor initiation. In preliminary studies, we found that inhibition of the Wnt pathway markedly reduced tumorsphere formation in five independent tumor derived cell lines (FIG. 9).

The relationship between levels of DKK3b expression and the number of cells showing the tumor initiating cell phenotype (CD49f$^{high}$, CD24$^{low}$, CD61$^+$) in tumors are used to identify the impact of DKK3b on tumor-initiating cells from the TBP mouse. The DKK3b and β-catenin levels in flow-sorted cells are assayed by qPCR and immunoblotting. We expect tumor-initiating cells to have lower levels of DKK3b expression than the remaining cell population.

Next, we will establish the basal tumor initiating capacity of (CD49f$^+$, CD44$^+$, CD24$^-$, EpCAM$^+$) sorted primary human epithelial tumor cells. Cells will be prepared from freshly harvested human tumor samples (UMass Tumor Bank) and in vitro (soft agar/tumorsphere) and in vivo (transplant) assays done as detailed above. Sorted cell populations will be manipulated by viral delivery of Dkk3b cDNA (over-expression) or RNAi (knockdown) and the impact altered DKK3b expression on tumorigenesis systematically determined.

Figure 10:
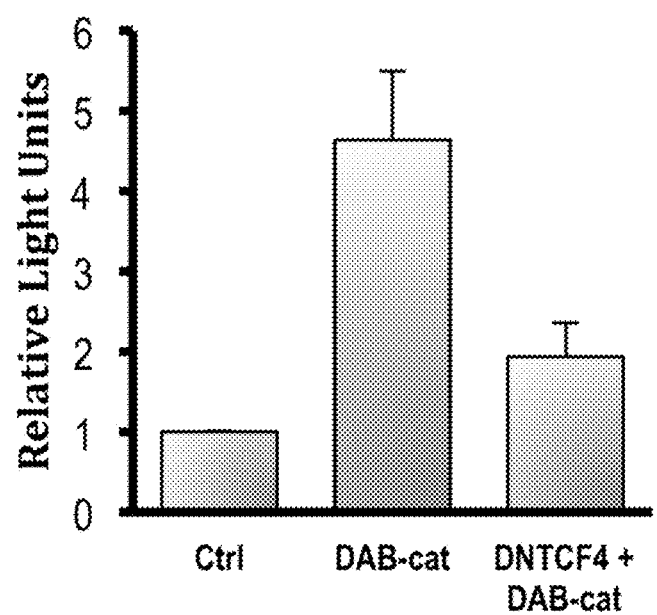
FIG. 10 depicts exemplary dominantly active β-catenin (DA-cat) eliciting TOPFLASH activity in mouse tumor-derived cells (line 1029) and is repressed by dominant negative effector, TCF4 (DNTCF4).
Figure 11:
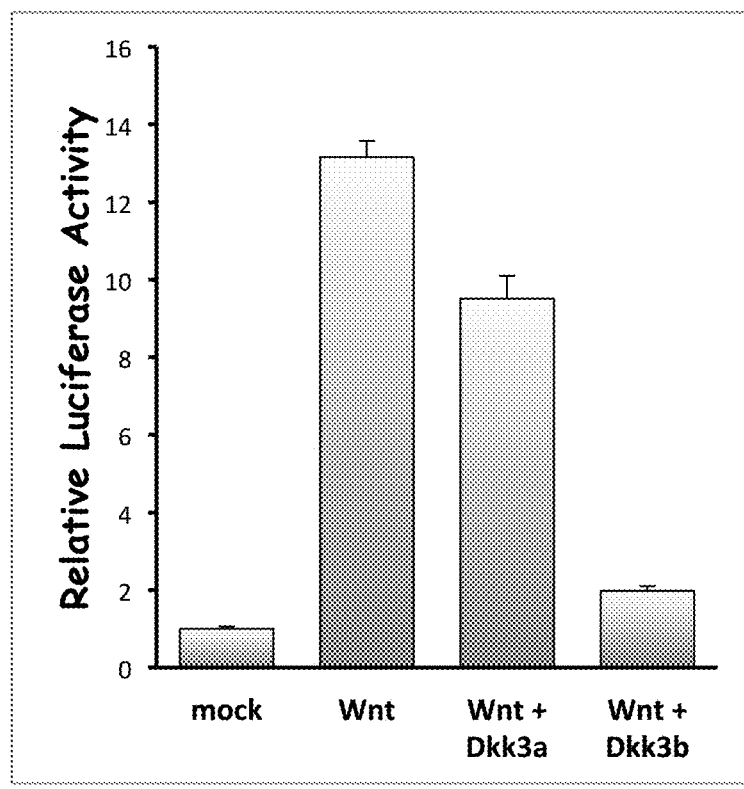
FIG. 11 depicts exemplary NMuMG cells that were transfected with Wnt7a, DKK3a and DKK3b and grown for 48 hr. Cell lysates were prepared in triplicate and luciferase expression determined using standard laboratory methods.

Demonstrate That Exogenous DKK3b Expression in Established Tumors Causes Tumor Regression Our murine model of transplanted cancer is modified to include TBP-derived tumor cells that express TCF-driven TOPFlash, and a tet-inducible DKK3b. These reporter cells allow us to visualize Wnt stimulated tumor growth in a living mouse. DKK3b expression are induced by oral, IP, or direct tumor injection of tetracycline at different stages of tumor growth and tumor size is monitored by live animal imaging using the Xenogen® IVIS imaging system. Using this approach we can directly relate DKK3b expression to pathway-specific changes in tumor cell Wnt signaling and tumor regression. In vitro pilot studies show that Wnt-dependent luciferase expression was repressed by blocking TCF signaling (FIG. 10).

Methods and Procedures

Histology.
Standard immunohistochemical and immunofluorescent techniques are used to analyze mammary tissue morphology as detailed herein.

FACS.
Markers of tumor initiating cells have been reported for mice (CD49f$^{high}$, CD24$^{low}$, CD61$^+$) and human breast cancers (CD49f$^+$, CD44$^+$, CD24$^-$, EpCAM$^+$). All antibodies are commercially available.

Tumorsphere Assay.
Tumor cells are grown in non-adherent conditions (ultra low attachment plates, Corning) in defined medium containing EGF and FGF. Mouse tumorsphere-forming units (TFU) are determined by counting. (Liu, et al. 2007 *Cancer research* 67 (18):8671-8681.) The time to generation and the total number of tumorspheres are the two parameters used as the assay readout.

Cell Suspension and Transplantation.
To explore the ability of DKK3b to regress established tumors, a key property of any therapeutic target, TBP cells harboring a TCF-driven TOPFlash reporter are generated that express DKK3b or GFP (control) under control of a tetracycline-inducible promoter. Cells are injected into the mammary fat pads of syngeneic (FVB) recipient mice. A TBP cell line is also produced that also carries a stably integrated TOPFlash luciferase reporter (M50 Super 8× TOPFlash), driven by eight copies of the optimized TCF-binding element (FIG. 10).

For transplantation, 1×10$^6$ cells are mixed 1:1 with Matrigel and injected into the #2 mammary gland of recipient 7-8 week old FVB mice. Tetracycline is given by the drinking water, IP injection, direct tumor injection, based on the optimal delivery method, when tumors reach 0.5 cm in diameter as measured using calipers. Tumor growth is monitored weekly by Xenogen® IVIS imaging system as detailed herein. When control tumors reach ~1.5 cm in diameter, tumors will be excised and DKK3b affected signaling pathways characterized. Power calculations indicated that groups of 10-11 injected mice for each cell line are sufficient to achieve statistically significant results.

Statistics and Power Analysis.
Statistical methods and power analyses are described herein.

Interrupting Wnt signaling by reducing the fold-change of cytoplasmic β-catenin has important translational implications as a novel regulatory pathway that can halt expansion of the mammary tumor-initiating cell. From this point of view, re-expression of DKK3b, either by in situ activation through its native promoter or by transfection of Dkk3b cDNA will attenuate anchorage-independent growth of mammary epithelial cells and block formation of tumorspheres, a property correlated with in vivo tumor initiation capacity. (Liu, et al. 2007 *Cancer research* 67 (18):8671-8681.) The experiments described are straightforward in design, validated by assay, and provide the experimental foundation for the therapeutic application of DKK3b for tumor regression. In the in vivo experiments, we expect loss of DKK3b to aggravate Wnt1 tumorigenesis, but this requires inactivation of both alleles that may have untoward consequences. To avoid this, tumor specific DKK3b knockdown is done by tumor delivery of lentiviral siRNA, a means of generating tissue targeted DKK3b deletion mutants for analysis of Wnt1-based tumor evolution.

ZFN-Based Gene Editing in Producing DKK3b Reporter Mouse and Any Promoter Function Studies The zinc-finger nuclease (ZFN)-based gene editing approach is used to produce a Dkk3b reporter mouse by redirecting the DKK3b promoter to drive expression of a fluorescent reporter (FIG. 4).

During validation of the ZFN pairs, gene-edited, Dkk3b-promoter driven CFP C8 (C8Dkk3b$^{CFP+/-}$) cells are generated by default. The C8 astrocyte is an immortal cell line with suppressed Dkk3 gene expression and can be used to explore the cellular event(s) impacted by DKK3b without the confounding impact of aneuploidy/polyploidy and the genetic instability inherent in tumor cell lines. Moreover, this cell line is an invaluable resource for promoter function studies. Systematic functional analysis of the Dkk3b promoter is done to identify individual Dkk3b promoter elements using CFP expression as the endpoint and in silico analysis (TranFac, Genomatrix algorithms) of promoter element(s). One or more promoter modulators that increase transcription from this locus are identified using this promoter surveillance approach.

The gene edited Dkk3b locus is markedly "silenced" by hypermethylation in the immortalized C8 cells. Methylase inhibitors and deacetylation activators were used to increase expression from this promoter. As shown in FIG. 12, the gene edited C8$^{Dkk3bCFP+/-}$ cells expressed weak CFP signals, while inhibition of methylation markedly increased reporter expression. These data validate the ZFN targeting strategy, confirm CFP insertion and show that methylase inhibitors can derepress the "silenced" DKK3 promoter.

Figure 13:
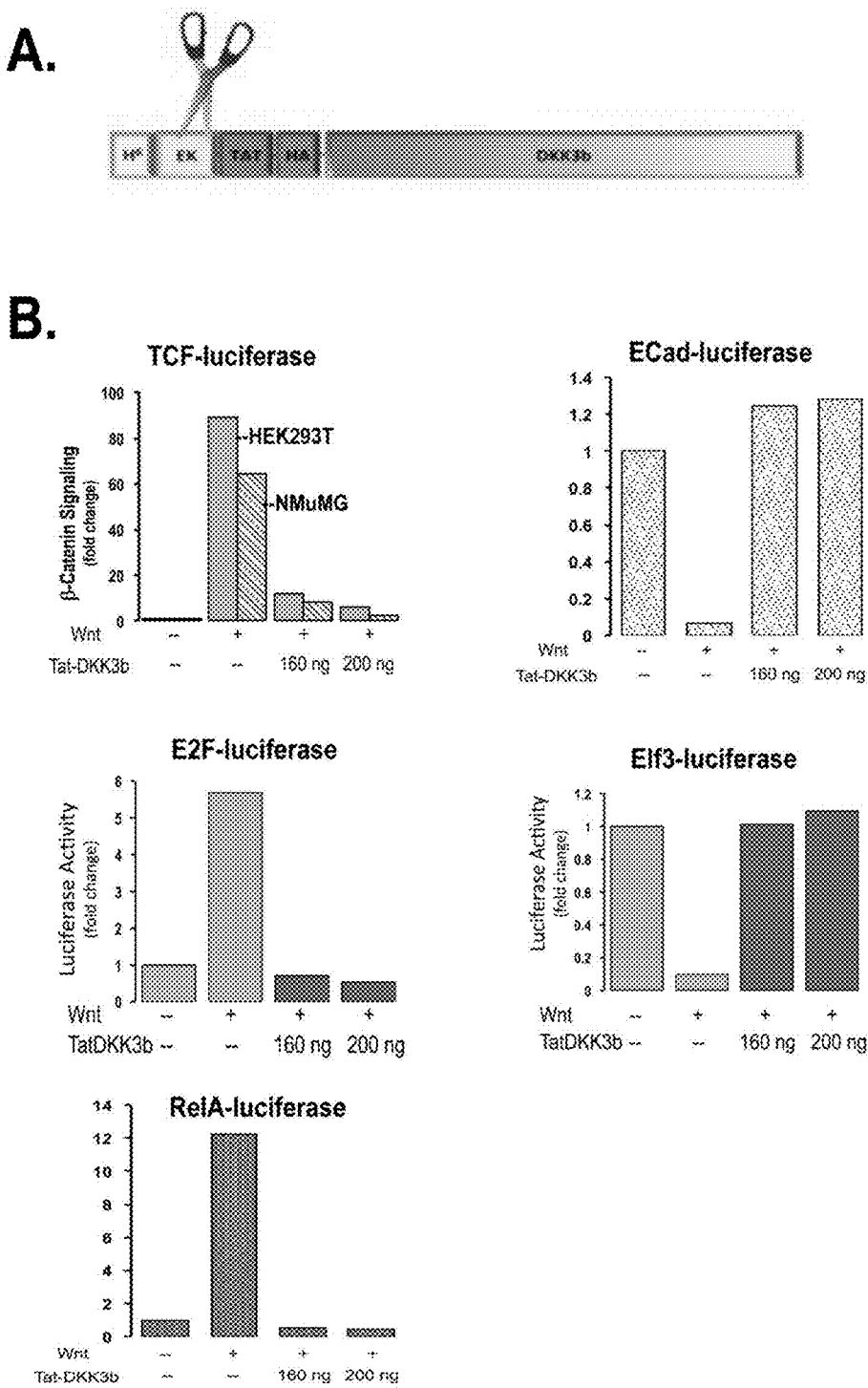
FIG. 13 depicts exemplary, A. Domain organization of the TAT-DKK3b fusion protein. B. Effects of TAT-DKK3b on b-catenin dependent gene expression in Wnt-treated HEK293T or NMuMG cells. Cell were transfected with plasmid cocktails containing Wnt, promoter-luciferase, and a transfection control, pRhluc. Cells were exposed to TAT-DKK3b for 5 min and grown for 24 h; lysates were made and luciferase activity determined.
Figure 14:
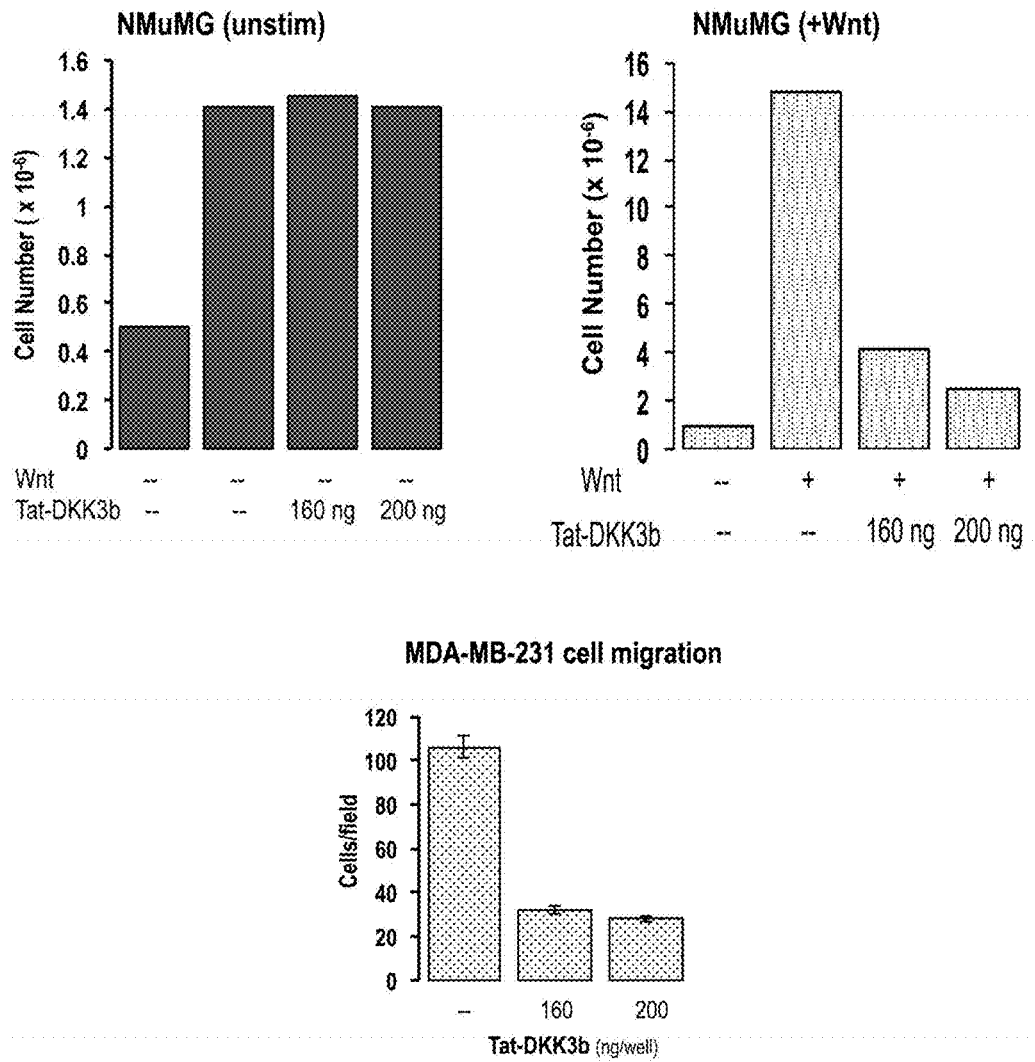
FIG. 14 depicts exemplary effects of TAT-DKK3b on cell proliferation and metastasis.
Figure 15:
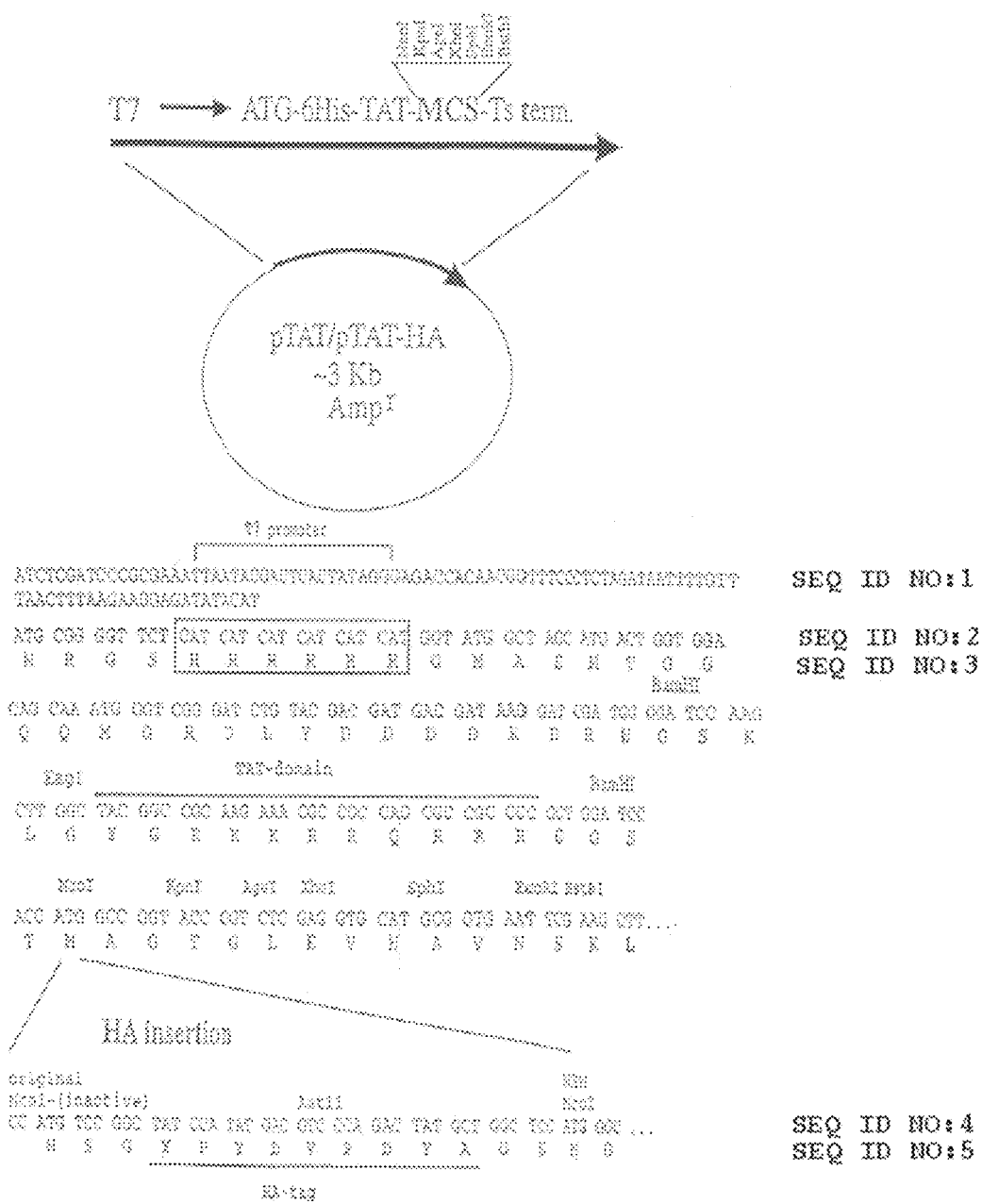
FIG. 15 depicts exemplary pTAT/pTAT-HA construct.
Figure 18:
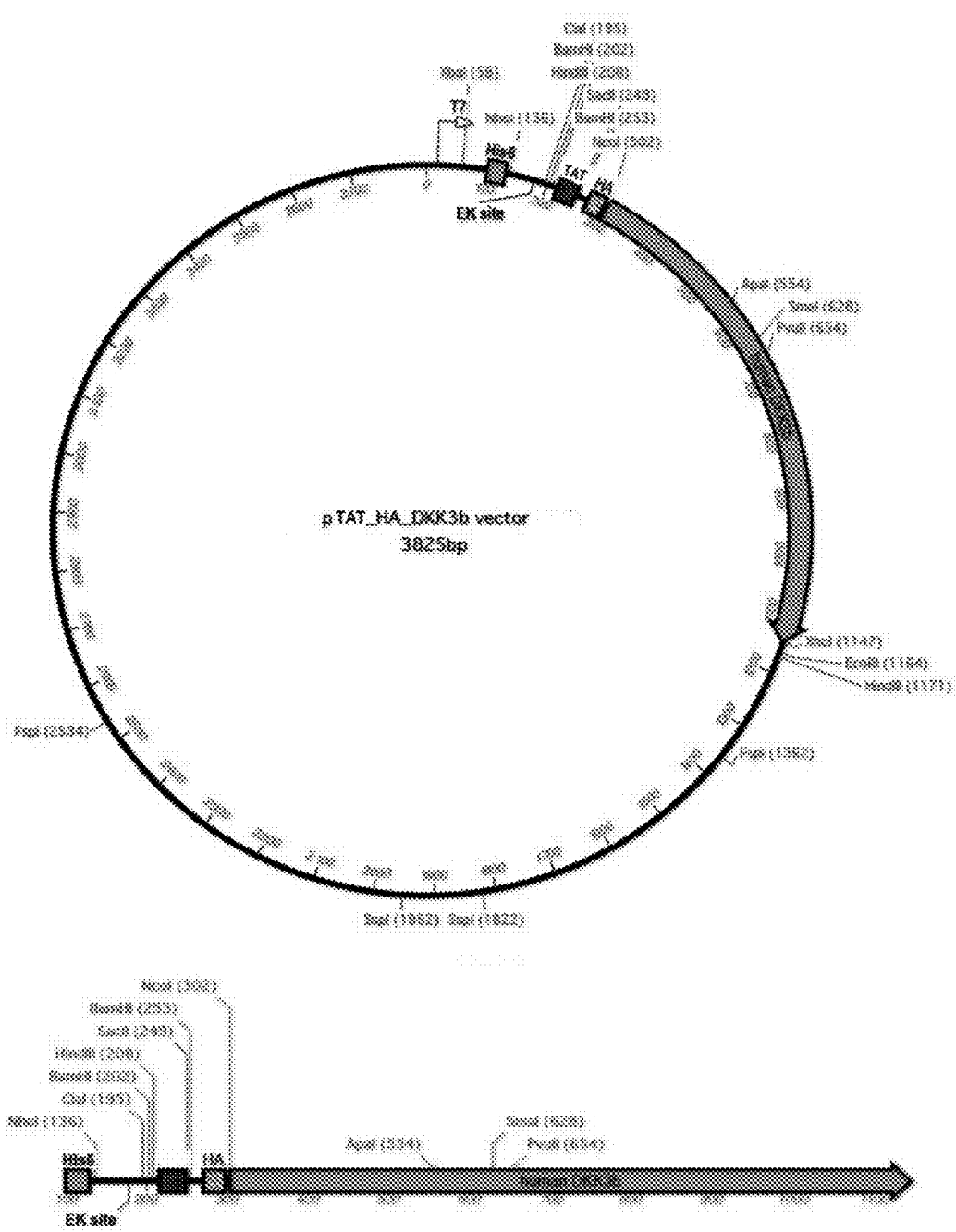
FIG. 18 depicts exemplary original TAT-HA Construct.
Figure 19:
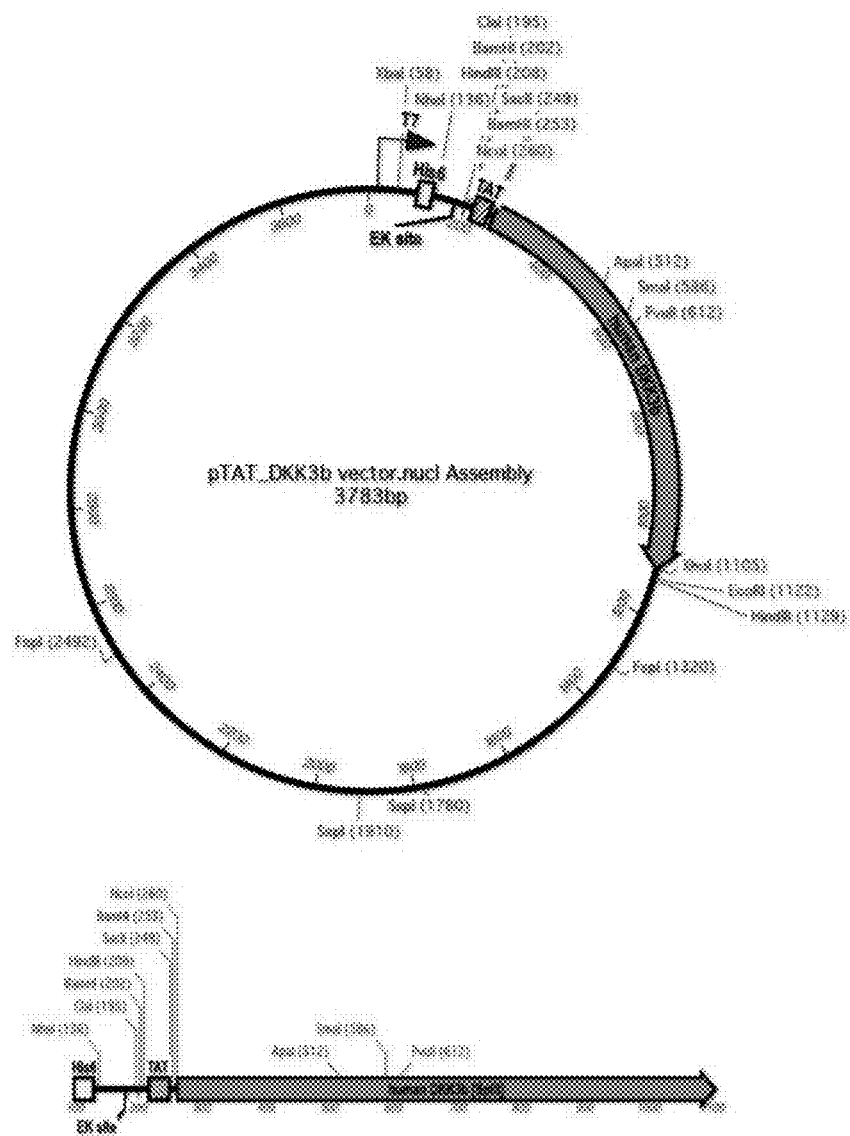
FIG. 19 depicts exemplary optimized TAT.
Figure 20:
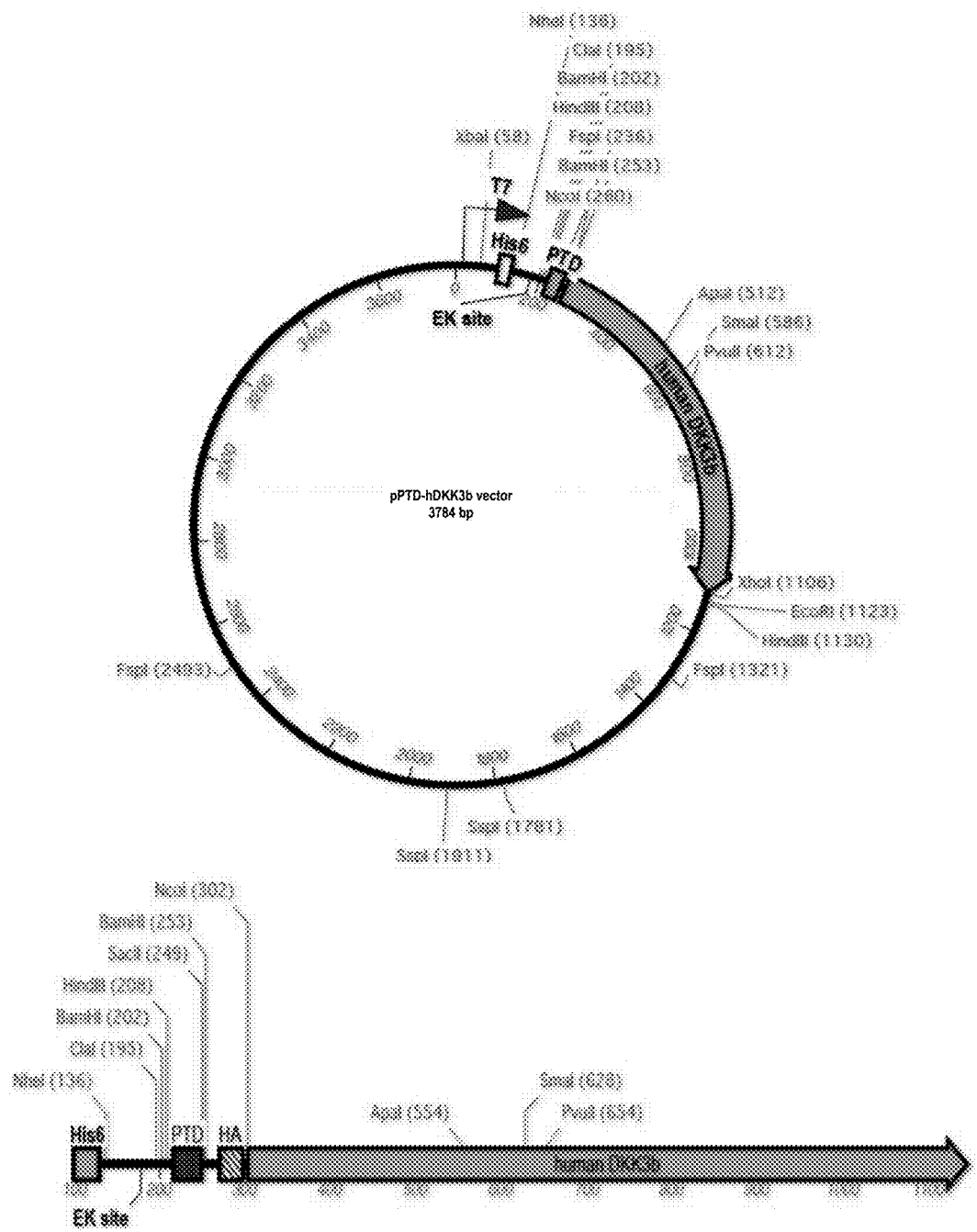
FIG. 20 depicts exemplary optimized PTD Construct.
Figure 22:
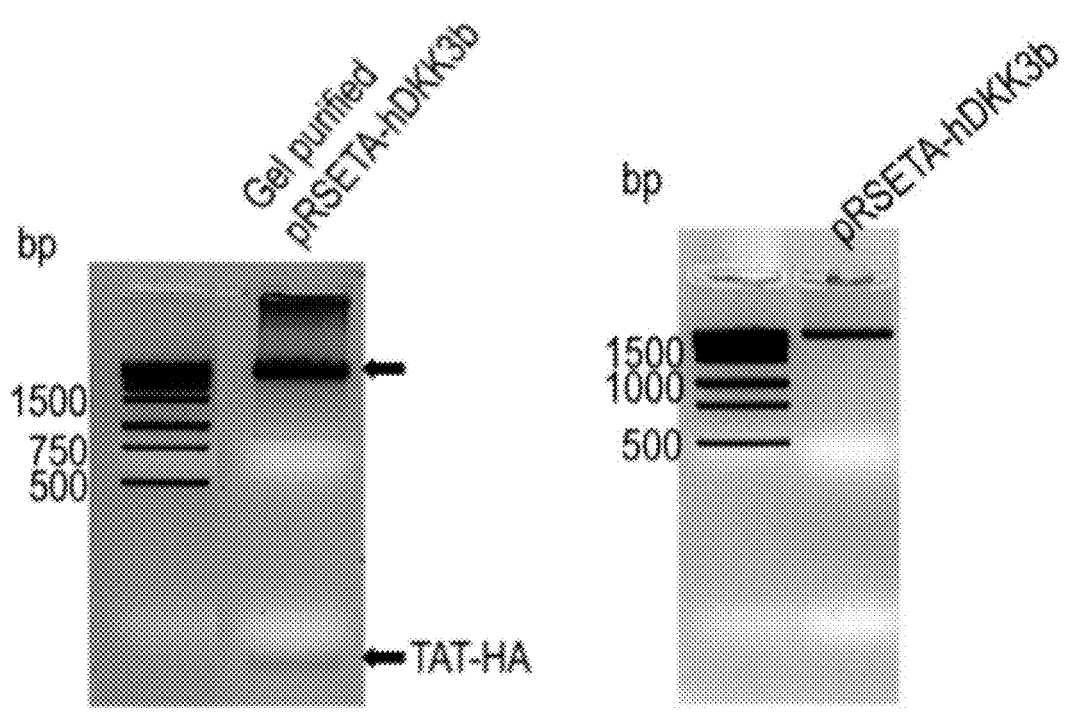
FIG. 22 depicts exemplary gel-purified pRSETA-hDKK3b.

DKK3b Fusion Protein and Effects on Beta-Catenin Dependent Gene Expression, Cell Proliferation and Metastasis Small membrane transduction domains (MTD) are fused to the N-terminus of DKK3b to produce a bioavailable fusion protein using published methods. (Nagahara, et al. 1998 Nature medicine 4 (12):1449-52). A TAT-DKK3b fusion construct was assembled and purified the fusion protein from urea-denatured bacterial lysates using Ni-NTA resins. FIG. 13A shows the epitope domains of the TAT-DKK3b fusion protein. As shown in FIG. 13B, a 5 min treatment of Wnt-stimulated NMuMG and HEK293T cells with TAT-DKK3b (≥40 fg/cell) silenced β-catenin-dependent TCF-, E2F- and RelA-driven gene expression and restored expression of β-catenin-suppressed markers of cellular differentiation, E-cadherin and Elf3 (FIG. 13B). The data in FIG. 14 shows that TAT-DKK3b treatment had no effect on untransformed NMuMG cells, but arrested cell proliferation of Wnt-stimulated cells. TAT-DKK3b also blocked migration of the highly invasive human MDA-MB-231 breast cancer cells. These data show that the bacterially expressed, membrane-permeant DKK3b retains all of the anti-cancer properties of native DKK3b.

The TAT-HA-DKK3b fusion protein used in initial studies included epitope tags and ancillary sequence that comprised almost 25% of the fusion protein and are undesirable in a therapeutic product. To reduce antigenicity and eliminate unnecessary sequence, the TAT-HA cassette is replaced with an 11 residue long synthetic MTD reported to increase membrane permeability by >30 fold reduce/eliminate antigenicity and to extend the biological half-life of the encoded fusion protein. The optimized MTD-DKK3b will retain the polyHistidine tag for purification of the MTD-DKK3b under denaturing conditions.

Optimize Conditions for Production of MTD-DKK3b in Bacteria.

Small cultures of the individual pMTD-DKK3b constructs are prepared in IPTG-inducible, T7 polymerase expressing E. coli. IPTG-induction/growth conditions are chosen so that >90% of the MTD-DKK3b is localized to inclusion bodies. Bacterial cells are urea extracted, MTD-DKK3b purified by Ni++ affinity isolation and then formulated without urea. MTD-DKK3b expression levels are evaluated by immunoblot analysis using anti-polyHis or anti-DKK3b antibodies. Purified candidate MTD-DKK3bs are tested for purity by SDS-PAGE and SEC-HPLC, and for bioactivity using reporter cell lines that secrete b-catenin dependent reporters into the growth medium (see below). The optimal clone are used to produce a Master Cell Bank for future clinical development.

Develop Purification Scheme for Unfolded MTD-DKK3b Using GMP Standards.

Bacterial cell lysis and isolation of the MTD-DKK3b from inclusion bodies are systematically optimized. The concentration of denaturants, urea and/or chaotropic salts, lytic conditions and cleanup steps are systemically examined. Urea concentrations are optimized for maximum recovery of the fusion protein while minimizing the urea content of the extraction buffers for ease of purification scalability.

Urea extracted proteins are affinity purified on Ni$^{++}$ resins and eluted with imidazole in buffered urea. Urea is then rapidly removed to minimize refolding of the MTD-DKK3b fusion protein. Optimization of purification at this stage primarily involves investigation of washing steps while the protein is bound to the Ni$^{++}$ resin with variable wash buffer pH and imidazole concentrations. A key parameter at this stage is the reduction of contamination. Bioactivity of the purified MTD-DKK3b is evaluated b-catenin dependent reporter cell lines. Refolding and aggregation are monitored by fluorescent dye binding.

Further information on assembly of TAT/PTD DKK3b are provided in FIGS. 15-22.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. An isolated fusion protein comprising a membrane transduction domain (MTD) peptide fused to the N-terminus of the human intracellular Dickkopf (Dkk3) protein encoded by exons 3-8 of the human Dkk3 gene locus.

2. The fusion protein of claim 1 wherein the fusion protein in purified.

3. The fusion protein of claim 1 wherein the MTD comprises the amino acids 5-15 of SEQ ID NO: 7.

4. The fusion protein of claim 1 wherein the MTD comprises TAT.

5. An isolated nucleic acid encoding the fusion protein of claim 1.

6. An isolated nucleic acid encoding the fusion protein of claim 3.

7. A recombinant vector comprising the nucleic acid of claim 5 or 6.

8. An isolated host cell transformed with the recombinant vector of claim 7.

9. The host cell of claim 8 wherein the host cell is a bacterial cell or a mammalian host.

* * * * *